(12) United States Patent
Ternes et al.

(10) Patent No.: US 11,207,528 B2
(45) Date of Patent: Dec. 28, 2021

(54) ATRIOVENTRICULAR CONDUCTION GUIDED HIS-BUNDLE PACING

(71) Applicant: Cardiac Pacemakers, Inc., St. Paul, MN (US)

(72) Inventors: David J. Ternes, Roseville, MN (US); Deepa Mahajan, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 10 days.

(21) Appl. No.: 16/707,550

(22) Filed: Dec. 9, 2019

(65) Prior Publication Data

US 2020/0179705 A1 Jun. 11, 2020

Related U.S. Application Data

(60) Provisional application No. 62/777,564, filed on Dec. 10, 2018.

(51) Int. Cl.
*A61N 1/368* (2006.01)
*A61N 1/37* (2006.01)
*A61N 1/365* (2006.01)

(52) U.S. Cl.
CPC ..... *A61N 1/36585* (2013.01); *A61N 1/36842* (2017.08); *A61N 1/3702* (2013.01); *A61N 1/3682* (2013.01)

(58) Field of Classification Search
CPC .............. A61N 1/36585; A61N 1/3682; A61N 1/36842; A61N 1/3702
See application file for complete search history.

(56) References Cited

U.S. PATENT DOCUMENTS

| | | | |
|---|---|---|---|
| 7,218,965 B2 | 5/2007 | Casavant et al. | |
| 8,588,907 B2 | 11/2013 | Arcot-Krishnamurthy et al. | |
| 8,880,169 B2* | 11/2014 | Zhu | A61N 1/3627 607/9 |
| 2004/0215262 A1* | 10/2004 | Ferek-Petric | A61N 1/368 607/17 |
| 2006/0224197 A1* | 10/2006 | Havel | A61N 1/3627 607/9 |
| 2016/0213272 A1* | 7/2016 | Pujar | A61B 5/6852 |
| 2018/0104502 A1* | 4/2018 | Perschbacher | A61N 1/3925 |
| 2019/0111270 A1* | 4/2019 | Zhou | A61N 1/36507 |
| 2019/0126090 A1* | 5/2019 | O'Connor | A63B 24/0087 |
| 2019/0134405 A1* | 5/2019 | Sheldon | A61B 5/361 |
| 2020/0179692 A1* | 6/2020 | Ternes | A61N 1/3624 |

* cited by examiner

*Primary Examiner* — Brian T Gedeon
(74) *Attorney, Agent, or Firm* — Schwegman Lundberg & Woessner, P.A.

(57) ABSTRACT

Systems and methods for dynamically controlling HBP delivery based on patient AV conduction status are disclosed. An exemplary medical system includes an electrostimulation circuit to generate HBP pulses to stimulate a His bundle or a bundle branch of the heart. An AV conduction monitor circuit continuously or periodically assesses AV conduction status, and detects an indication of presence or absence of AV conduction abnormality. If an AV conduction abnormality is indicated, a control circuit may control the electrostimulation circuit to deliver the HBP pulses. Ventricular backup pacing may be delivered if HBP fails to capture and elicit ventricular activation. When the AV conduction become normal, the control circuit may withhold HBP delivery and promote patient intrinsic ventricular activation.

20 Claims, 7 Drawing Sheets

ATRIOVENTRICULAR CONDUCTION GUIDED HIS-BUNDLE PACING

CLAIM OF PRIORITY

This application claims the benefit of priority under 35 U.S.C. § 119(e) of U.S. Provisional Patent Application Ser. No. 62/777,564, filed on Dec. 10, 2018, which is herein incorporated by reference in its entirety.

TECHNICAL FIELD

This document relates generally to medical systems, and more particularly, to systems, devices and methods for pacing of cardiac conductive tissue, such as a His bundle or a bundle branch.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, which propagate through natural electrical conduction pathways known as His-Purkinje system to various regions of the heart to excite the myocardial tissue of the heart. For example, the action potentials originated from the SA node propagate through the atrioventricular (AV) node, the His bundle (also known as Bundle of His), the bundle branches, and Purkinje fibers to reach the ventricular myocardium, resulting in coordinated contractions in both ventricles.

Coordinated delays in the propagation of the action potentials in a normal electrical conduction system cause the various portions of the heart to contract in synchrony to result in efficient pumping functions. A blocked or otherwise abnormal electrical conduction and/or deteriorated myocardium may cause dyssynchronous contraction of the heart, resulting in poor hemodynamic performance, including a diminished blood supply to the heart and the rest of the body. For example, an abnormal delay in the transmission of the action potentials in the His bundle may cause irregular or dyssynchronous contractions of the ventricles, resulting in an abnormal rhythm of the heart.

Artificial cardiac pacing system have been used to rectify cardiac dyssynchrony and to improve hemodynamic performance. The artificial cardiac pacing system may provide electrical stimulations to one or more portions of the heart such as to restore normal functioning of the heart to a certain extent. For example, right ventricular pacing via electrodes implanted in the apex of the RV have been used in both single ventricular and biventricular (BiV) pacing. RV apex pacing directly excites the ventricular myocardium, rather than propagating the action potentials through the natural conduction pathways. Studies have shown that, in some patients, long-term RV apex pacing may result in loss of synchronous mechanical contraction of RV and LV, partially due to the interventricular delay in impulse propagation to the left ventricle. Consequently, permanent changes in myocardial perfusion and structure may develop over time in these patients, which may further decrease cardiac output and deteriorate ventricular function. BiV pacing involves RV pacing via one lead, and LV pacing via another lead, and has been demonstrated to restore synchronized contraction of both ventricles. However, the potential adverse impact on ventricular function produced by the RV apex pacing may still exist in BiV pacing. Additionally, compared to cardiac depolarization through AV node activation and propagation through the natural conduction pathways, the BiV pacing may not produce similarly coordinated cardiac contractions. Moreover, the surgical procedure for placing the LV lead through the coronary sinus and into a vein on the left ventricular wall may be complex and challenging in some patients.

Overview

This document discusses systems, devices, and methods for dynamic control of His-bundle pacing (HBP) according to patient AV conduction status. An exemplary medical system includes an electrostimulation circuit to generate pacing pulses to stimulate a His bundle, or a bundle branch of the heart (e.g., left bundle branch), among other portions of patient physiologic conduction pathway. The system includes an AV conduction monitor circuit to continuously or periodically assess patient AV conduction status, and detect an indication of presence or absence of AV conduction abnormality. In the event that an AV conduction abnormality is indicated, a control circuit may control the electrostimulation circuit to deliver the HBP pulses to stimulate the physiologic conduction pathway. Ventricular backup pacing may be delivered if HBP fails to capture and elicit ventricular activation. If AV conduction status becomes normal, the control circuit may withhold delivery of the HBP pulses to promote intrinsic ventricular conduction and activation.

Example 1 is a medical-device system for pacing a physiologic conduction pathway including a His bundle or a bundle branch of the heart. The system comprises an atrioventricular (AV) conduction monitor circuit configured to detect an indication of a presence or absence of AV conduction abnormality of a heart of a subject; and a control circuit control circuit configured to control an electrostimulation circuit configured to generate His-bundle pacing (HBP) pulses, and to provide a control signal to, in response to a detected indication of presence of AV conduction abnormality of the heart, deliver the generated HBP pulses to stimulate a physiologic conduction pathway of the heart, and in response to a detected indication of absence of AV conduction abnormality of the heart, withhold delivery of the HBP pulses.

In Example 2, the subject matter of Example 1 optionally includes the electrostimulation circuit, and control circuit is configured to sense an intrinsic ventricular activation during a first atrioventricular delay (AVD) that begins at the atrial sensed event or the atrial paced event, and the electrostimulation circuit that can be configured to deliver ventricular demand pacing (VDP) at expiration of the first AVD if no intrinsic ventricular activation is sensed during the first AVD.

In Example 3, the subject matter of any one or more of Examples 1-2 optionally includes the control circuit that can be further configured to, in response to the indication of presence of AV conduction abnormality, time the delivery of HBP pulses at expiration of an atrio-Hisian delay (AHD), sense a ventricular activation during a second atrioventricular delay (AVD), and time delivery of ventricular backup pacing (VBP) at expiration of the second AVD if no ventricular activation is sensed during the second AVD. Both the AHD and AVD can begin at an atrial sensed event or an atrial paced event, and the AVD is longer than the AHD.

In Example 4, the subject matter of Example 3 optionally includes the control circuit that can be configured to determine a frequency of VBP delivery over a specified time period, and to optimize an HBP configuration for stimulating the physiologic conduction pathway if the determined VBP frequency exceeds a threshold.

In Example 5, the subject matter of Example 4 optionally includes the control circuit that can be configured to optimize the HBP configuration which can include verifying a HBP capture status; extending the second AVD if the HBP capture status is a selective or non-selective His bundle capture; and adjusting an HBP parameter if the HBP capture status is a para-Hisian capture or a loss of capture.

In Example 6, the subject matter of Example 5 optionally includes the control circuit that can be configured to perform a threshold test to determine an HBP threshold, and to adjust the HBP parameter using the determined HBP threshold.

In Example 7, the subject matter of any one or more of Examples 4-6 optionally includes the AV conduction monitor circuit that can be configured to periodically assess AV conduction status if the frequency of VBP falls below the threshold, the assessment including detecting the indication of presence or absence of AV conduction abnormality.

In Example 8, the subject matter of any one or more of Examples 1-7 optionally includes the AV conduction monitor circuit that can be configured to measure a sensed AV interval (AVIS) between an atrial sensed event and a ventricular sensed event; and the control circuit that can be configured to control the electrostimulation circuit to: if the AVIS exceeds a sensed AVI threshold, deliver the HBP pulses at expiration of a sensed atrio-Hisian delay (AHDS) that begins at the atrial sensed event; and if the AVIS falls below the sensed AVI threshold, withhold delivery of the HBP pulses, and deliver ventricular demand pacing (VDP) at expiration of a sensed atrioventricular delay that begins at the atrial sensed event.

In Example 9, the subject matter of any one or more of Examples 1-8 optionally includes the AV conduction monitor circuit that can be configured to measure a paced AV interval ($AVI_P$) between an atrial paced event and a ventricular sensed event; and the control circuit that can be configured to control the electrostimulation circuit to: if the $AVI_P$ exceeds a paced AVI threshold, deliver the HBP pulses at expiration of a paced atrio-Hisian delay ($AHD_P$) that begins at the atrial paced event; and if the $AVI_P$ falls below the paced AVI threshold, withhold delivery of HBP pulses, and deliver ventricular demand pacing (VDP) at expiration of a paced atrioventricular delay that begins at the atrial paced event.

In Example 10, the subject matter of any one or more of Examples 1-9 optionally includes the AV conduction monitor circuit that can be configured to detect an AV block pattern, and the control circuit is configured to time the delivery of HBP pulses in accordance with the detected AV block pattern.

In Example 11, the subject matter of Example 10 optionally includes the AV conduction monitor circuit that can be configured to determine a target AV interval (AVI) corresponding to the detected AV block pattern using a plurality of AV intervals prior to a conduction block to the ventricle; and the control circuit that can be configured to determine an atrio-Hisian delay (AHD) using the target AVI and a His-to-ventricular interval (HVI), and to time the delivery of the HBP pulses at expiration of the determined AHD.

In Example 12, the subject matter of Example 11 optionally includes the AV block pattern that can be a Mobitz type I block, and the target AVI can be a shortest interval among a plurality of progressively prolonged AV intervals prior to the conduction block to the ventricle.

In Example 13, the subject matter of Example 11 optionally includes the AV block pattern that can be a Mobitz type II block, and the target AVI can be a central tendency of the plurality of conducted AV intervals prior to a conduction block.

In Example 14, the subject matter of Example 11 optionally includes the AV block pattern Example 11 a Mobitz type II block, and the AV conduction monitor circuit can be configured to generate a statistic of conducted beats prior to a conduction block to the ventricle; and the control circuit can be configured to control the electrostimulation circuit to deliver the HBP pulses for a first number of consecutive cardiac cycles followed by withholding the HBP delivery for a second number of cardiac cycles. The first and second numbers can be each determined using the generated statistic of conducted beats.

In Example 15, the subject matter of any one or more of Examples 11-14 optionally includes the control circuit that can be further configured to determine a second atrioventricular delay (AVD) using the target AVI, and to time the delivery of ventricular backup pacing (VBP) pulses at expiration of the second AVD if no ventricular activation is sensed during the second AVD.

Example 16 is a method for pacing a physiologic conduction pathway including a His bundle or a bundle branch of the heart. The method comprises steps of: detecting an indication of presence or absence of AV conduction abnormality; in response to an indication of presence of AV conduction abnormality, delivering the HBP pulses to stimulate the physiologic conduction pathway; and in response to an indication of absence of AV conduction abnormality, withholding delivery of the HBP pulses, and delivering ventricular demand pacing (VDP) at expiration of a first AVD if no intrinsic ventricular activation is sensed during the first AVD.

In Example 17, the subject matter of Example 16 optionally includes, in response to the indication of presence of AV conduction abnormality, delivering the HBP pulses at expiration of an atrio-Hisian delay (AHD), sensing a ventricular activation during a second atrioventricular delay (AVD), and delivering ventricular backup pacing (VBP) at expiration of the second AVD if no ventricular activation is sensed during the second AVD. Both the AHD and AVD can begin at an atrial sensed event or an atrial paced event, and the AVD can be longer than the AHD.

In Example 18, the subject matter of Example 17 optionally includes determining a frequency of VBP delivery over a specified time period, and optimizing an HBP configuration for stimulating the physiologic conduction pathway if the determined VBP frequency exceeds a threshold.

In Example 19, the subject matter of Example 18 optionally includes optimizing the HBP configuration that can include verifying a HBP capture status; extending the second AVD if the HBP capture status is a selective or non-selective His bundle capture, and adjusting an HBP parameter if the HBP capture status is a para-Hisian capture or a loss of capture.

In Example 20, the subject matter of any one or more of Examples 16-19 optionally includes detecting an AV block pattern, and delivering the HBP pulses in accordance with the detected AV block pattern.

In Example 21, the subject matter of Example 20 optionally includes the AV block pattern that can be a Mobitz type I block, and the method comprises steps of determining a target AV interval (AVI) corresponding to a shortest interval among a plurality of progressively prolonged AV intervals prior to the conduction block to the ventricle; determining an atrio-Hisian delay (AHD) using the target AVI and a His-to-ventricular interval (HVI), and delivering the HBP pulses at expiration of the determined AHD.

In Example 22, the subject matter of Example 20 optionally includes the AV block pattern that can be a Mobitz type II block, and the method comprises steps of: generating a statistic of conducted beats prior to a conduction block to the ventricle; and delivering the HBP pulses for a first number of consecutive cardiac cycles followed by withholding the HBP delivery for a second number of cardiac cycles, the first and second numbers each determined using the generated statistic of conducted beats.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
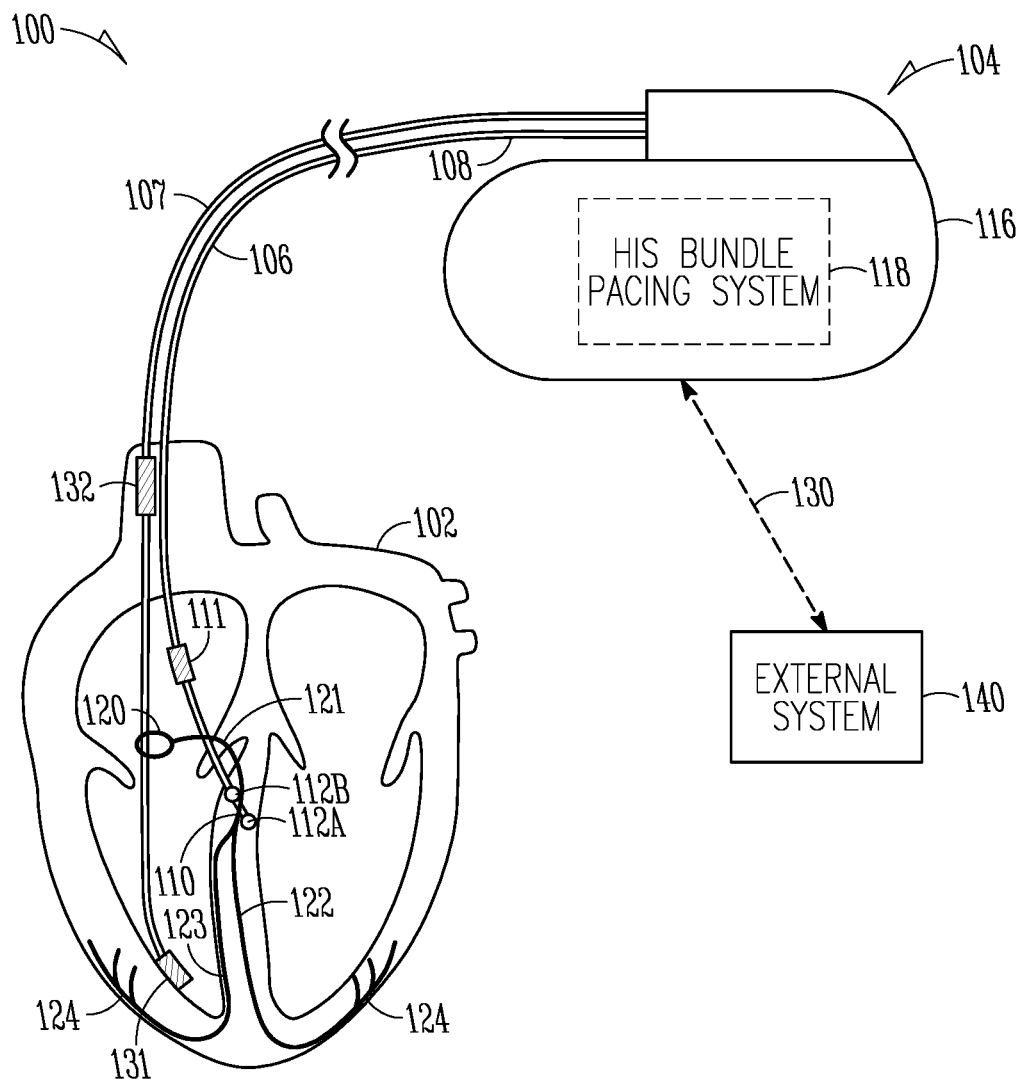
FIG. 1 illustrates generally an example of a cardiac disease management system and portions of an environment in which the system may operate.

Hemodynamic response to artificial pacing may depend on many factors, including pacing site selection and pacing configurations. Many patients receiving artificial pacing therapy have an intact His bundle and the natural cardiac electrical conduction system in the ventricles, and therefore having normal ventricular activation. Conventional cardiac pacing such as long-term RV apex pacing may cause a decrease in cardiac efficiency due to the uncoordinated contraction sequence, and eventually exhibit adverse long-term effects. Dyssynchronous contraction of the ventricles occurs during conventional RV pacing because the activation sequence may be much slower and propagate slowly from the right to the left ventricle across the interventricular septum, thereby causing ventricular dyssynchrony. This sequence of activation results in an uncoordinated contraction, which does not occur during biventricular activation through the natural conduction system of the heart. The cells of the natural conduction system may propagate an activation signal about four times faster than working myocardium. A cardiac rhythm or functional management device configured to pace the His bundle is an alternative to conventional ventricular pacing in some patients. His-bundle pacing (HBP) may activate the heart's natural His-Purkinje system in some patients, and produce efficient and coordinated cardiac contractions. The potentially long-term harmful hemodynamic effects that may occur from continuous RV apex pacing may also be eliminated or reduced.

However, when not being successful, the HBP may not adequately restore cardiac synchrony. In some instances, the electrical stimulation may lose its ability to activate (or capture) the His bundle, but only activates the para-Hisian myocardium surrounding the His bundle. Stimulating muscles near the His bundle may cause dyssynchronous patterns similar to RV apical pacing. This undesirable effect is referred to as para-Hisian capture. Simultaneous capture of the His bundle and para-Hisian muscle (also known as a non-selective His-bundle capture) may be as clinically effective as the His-bundle only capture absent of para-Hisian muscle capture (also known as a selective His-bundle capture). This is because the ventricles are activated predominately by the rapidly conducting natural conduction system. Another undesirable effect of HBP is known as a complete loss of capture (LOC), where the HBP pulses capture neither the para-Hisian myocardium nor the His bundle. Therefore, verification of His-bundle capture status may be an important function of an HBP device in monitoring and assessing HBP therapy efficacy.

The ability of HBP to restore cardiac synchrony may also be dependent on the pacing site relative to the blockage site along the His-Purkinje system, such as at the His bundle or a bundle branch. Ventricular dyssynchrony in many heart failure (HF) patients may be attributed to various degrees of left bundle branch block (LBBB), which causes delayed LV depolarization lagging behind RV depolarization. Effective propagation of the action potentials through the His-Purkinje system to restore cardiac synchrony may be achieved only if the HBP pulses are delivered distal to the blockage site. If the HBP pulses are delivered proximal to the blockage site, even if the proximal portion of the His bundle is activated, the action potential cannot bypass the blockage and propagate to the ventricles through the His-Purkinje system. Consequently, no cardiac synchrony may be restored.

Atrioventricular (AV) conduction disturbance refers to abnormal conduction or obstruction (i.e., block) in the AV node or in the His-Purkinje system below the AV node. The AV blocks may be classified as first, second, or third degree. First-degree AV block refers to AV conduction delay, usually in the AV node, manifest by a prolonged P wave to R wave interval greater than 200 milliseconds (msec) and is commonly due to a delay in the AV node irrespective of QRS width. Second-degree AV block may be divided into Mobitz type I (Wenckebach) or Mobitz type II. Mobitz type I is characterized by progressive PR prolongation with eventual block after a P wave (i.e., atrial impulse is not conducted and the QRS complex is dropped). The PR interval following the blocked P wave is shorter than the last conducted PR interval before the blocked P wave. After the dropped QRS complex, the PR interval resets and the cycle repeats. Mobitz type I usually occurs in the AV node. Mobitz type II, which is characterized by the abrupt failure of conduction after a P wave without preceding PR prolongation, usually represents conduction disease below the AV node. Typically, atrial impulses are intermittently non-conducted and QRS complexes dropped in a repeating cycle of every third (3:1 block) or fourth (4:1 block) P wave. Third-degree AV block refers to completed AV dissociation. There is no electrical communication between the atria and ventricles and no relationship between P waves and QRS complexes. Cardiac function is maintained by an escape junctional or ventricular pacemaker.

In some patients, the AV conduction disturbance may change over time, and/or affected by medication and patient condition. This may lead to intermittent rather than persistent AV conduction or AV obstruction. For example, in patients with rate-dependent left bundle branch block (LBBB), AV conduction abnormality may be present at times of fast heart rates, and diminishes at slower heart rates. The rate-dependent AV conduction abnormality may be due to by myocardial ischemia or refractoriness of the left bundle at faster heart rates. Considering that the success of HBP capture and its ability to restore cardiac synchrony (and potential side effects such as phrenic nerve stimulation or pain sensation) may vary from patient to patient and affected by many factors (e.g., pacing site, stimulation strength), it is desirable, at least in some instances, to limit HBP therapy to those cases where patient AV conduction is compromised. When the AV conduction becomes normal (e.g., AV interval falling within a specific range or become stable), HBP may be withheld to promote patient intrinsic ventricular activation, such as produced by sinus node or atrial activations that propagate to the ventricles.

For the foregoing reasons, the present inventors have recognized that there is an unmet need for an artificial pacing system to automatically adapt HBP delivery to patient AV conduction status. Disclosed herein are systems, devices, and methods for pacing cardiac conductive tissue based on patient AV conduction status. An exemplary medical system may generate HBP pulses to stimulate a His bundle or a bundle branch. The system may continuously or periodically assess AV conduction status, and detect an indication of AV conduction abnormality. If an AV conduction abnormality is indicated, the system may deliver the HBP pulses to stimulate the physiologic conduction pathway. Ventricular backup pacing may be delivered if HBP fails to capture and elicit ventricular activation. If AV conduction status becomes normal, the control circuit may withhold delivery of the HBP pulses to promote intrinsic ventricular conduction and activation.

The systems, devices, and methods discussed in this document may improve the technology of cardiac pacing in patients with cardiac disease, such as heart failure with intermittent AV conduction, yet with little to no additional cost or system complexity. HBP may activate natural His-Purkinje system, thereby preserving ventricular synchrony and improving cardiac performance without structural and functional impairment to the heart. The HBP as discussed in the present document cab leverage the electrophysiology of the His bundle region, and improves pacing efficiency utilizing the natural conduction mechanisms of the heart, while reducing long-term harmful hemodynamic effects associated with RV apex pacing.

Adapting HBP therapy to patient varying AV conduction status, as discussed herein, may improve therapy efficacy and patient outcome particularly for those presented with intermittent AV conduction disturbance, such as rate-dependent BBB. The AV conduction guided HBP may help avoid or reduce chances of HBP pulses competing with the intrinsic atrial impulses that propagate through the heart's naturally conduction system. Promoting the intrinsic ventricular activation in the event of normal AV conduction may not only avoid or reduce unnecessary pacing therapies, but may produce more favorable ventricular performance and hemodynamic outcome. The AV conduction status guided HBP may also help reduce pacing time and pacing energy, conserve battery power, and extend implantable device longevity. Device size may be reduced to achieve existing performance metrics.

While His-bundle pacing is specifically discussed in this document, this is meant only by way of example and not limitation. It is within the contemplation of the inventor, and within the scope of this document, that the systems, devices, and methods discussed herein may be applied to stimulate right or left bundle branches or fascicles, the Purkinje fibers, among other conductive cardiac tissue.

FIG. 1 is a schematic diagram illustrating an embodiment of a cardiac disease management system 100 and portions of an environment in which the system 100 may operate. The cardiac disease management system 100 may perform a range of activities, including remote patient monitoring, diagnosis of a disease condition, and providing a therapy to treat the disease condition and to improve patient outcome. In an example, the therapy may include His-bundle pacing (HBP). One or more of these activities may be performed proximal to a patient (e.g., in the patient's home or office), through a centralized server (e.g., in a hospital, clinic or physician's office), or through a remote workstation (e.g., a secure mobile computing device).

As illustrated in FIG. 1, the cardiac disease management system 100 may be coupled to a patient's heart 102. The cardiac disease management system 100 includes an ambulatory medical device (AMD) and a lead system, configured to treat one or more cardiac diseases, such as cardiac arrhythmias or heart failure. The AMD may be an implantable device subcutaneously implanted in a chest, abdomen, or other parts of the patient, a subcutaneous monitor or diagnostic device, or a wearable medical device such as a patch-based device or a smart wearable or accessory, among others. In the example as illustrated in FIG. 1, the AMD includes an implantable medical device (IMD) 104. Examples of the IMD 104 may include a pacemaker, a pacemaker/defibrillator, a cardiac resynchronization therapy (CRT) device, a cardiac remodeling control therapy device, a neuromodulator, a drug delivery device, a biological therapy device, or an implantable diagnostic device such as a cardiac monitor or a loop recorder, among other implantable devices.

The lead system may include one or more transvenously, subcutaneously, or non-invasively placed leads or catheters. Each lead or catheter may include one or more electrodes. The arrangements and uses of the lead system and the associated electrodes may be determined by patient need and capability of the IMD 104. The associated electrodes on the lead system may be positioned at the patient's thorax or abdomen to sense a physiological signal indicative of cardiac activity, or a physiological response to stimulation of a target tissue. The lead system may be surgically inserted into, or positioned on the surface of, a heart 102. The electrodes associated with the lead system may be disposed in a target site in a right atrium (RA), a right ventricle (RV), a left atrium (LA), or a left ventricle (LV), or other body parts. Stimulation energy may be delivered to a target site via one or more of these electrodes. Some electrodes may be used for sensing cardiac activity, such as an intrinsic or evoked cardiac electrical activity.

In the illustrated example, the lead system may include a lead 106 having a proximal end 108 configured to be connected to the IMD 104, and a distal end 110 that includes one or more electrodes configured to deliver stimulation energy, such as in a form of pacing pulses, to the His bundle 121. FIG. 1 illustrates, by way of example and not limitation, two electrodes including a tip electrode 112A and a ring electrode 112B. Additional electrodes may be included in the lead 106 for sensing electrical activity or for delivering stimulation energy. The lead 106 may be placed such that one or more electrodes, such as 112A-112B, are positioned in or on a His bundle 121, a region distal to the blocked or slowly conducting AV node and in the AV septum, an interventricular septum region, or a right atrial region near the His-bundle 121. Alternatively, one or more of the electrodes 112A-112B, or other electrodes on the lead 106, may be configured to stimulate a bundle branch, such as a left bundle branch or a right bundle branch. As part of the natural electrical conduction system of the heart 102, the His bundle 121 transmits the electrical impulses from the AV node 120 to the point of the apex of the fascicular branches via the left bundle branch 122 and the right bundle branch 123. Each of the left and right branch bundles leads to the Purkinje fibers 124, which provide electrical conduction to the ventricles, causing the ventricles to contract. In some examples, the lead 106 may be placed such that one or more electrodes associated with the lead 106, such as 112A-112B, are positioned at or near other parts of the natural conduction pathways, such as one of the bundle branches 122 or 123, the Purkinje fibers 124, or other conductive tissue, in addition to or in lieu of a region at or near the His bundle 121.

In an example, the lead 106 may be a single pass lead having a plurality electrodes for stimulating multiple cardiac sites, including electrodes disposed at or near the His bundle (e.g., the electrodes 112A-112B) and electrodes disposed in one or more of RA, RV, LA, or LV of the heart 102. In some examples, in addition to the lead 106, the lead system may include separate leads for placement in different heart chambers or sites, such as an RA lead having one or more RA electrodes to stimulate a portion of RA or to sense RA electrical activity, a RV lead having one or more RV electrodes to stimulate a portion of RV or to sense RV electrical activity, or an LV lead having one or more LV electrodes to stimulate a portion of LV or to sense LV activity. In some examples, the cardiac disease management system 100 may include one or more leadless stimulators/sensors untethered to a lead and in wireless communication with the IMD 104. The leadless stimulators/sensors may deliver electrostimulation, sense a physiological signal, such as cardiac electrical signals in response to cardiac stimulation, and transmit the sensed data to the IMD 104.

The IMD 104 may include a hermetically sealed housing 116 that houses one or more of an electrostimulation circuit, a sensing circuit, a control circuit, a communication circuit, and a battery, among other components. In an example, the IMD 104 includes a His-bundle pacing system 118 configured to generate His-bundle pacing (HBP) pulses to stimulate the His bundle 121, such as via the lead 106 and the associated electrodes 112A or 112B. The His-bundle pacing system 118 may be programmed to deliver unipolar His-bundle pacing, where the pacing energy (current or voltage) is applied between one of the electrodes 112A-112B (e.g., as a cathode) and the housing 116 (e.g., as an anode). Alternatively, the His-bundle pacing system 118 may be programmed to deliver bipolar His-bundle pacing, where the pacing energy (current or voltage) is applied between two electrodes positioned at or near the His bundle, such as between the electrodes 112A and 112B. In some examples, electrodes used for unipolar or multipolar (e.g., bipolar or quadripolar) His-bundle pacing may be selected by a system user from a plurality of candidate electrodes from a given lead or multiple separate leads comprising the pacing system, and programmed into the His-bundle pacing system 118. In some examples, HBP pulses may be provide by a leadless device, such as a leadless cardiac pacemakers (LCP). One or more electrodes may be distributed on the body of the LCP and in contact with His-bundle region to deliver the HBP pulses.

The His-bundle pacing system 118 may sense a physiological signal using one or more electrodes associated with the lead system or a physiological sensor. Examples of the physiological signal may include an electrocardiogram (ECG), an intracardiac electrogram (EGM) such as an atrial EGM, a ventricular EGM, or a His bundle EGM, an thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, an intracardiac acceleration signal, a respiration signal, or a physical activity or exertion level signal, among others. In some examples, the His-bundle pacing system 118 may sense far-field ventricular activation (FFVA) using one or more electrodes or a physiologic sensor. The FFVA may be a signal recorded from afar at a given moment in time by two electrodes having similar source impedance. The FFVA may be sensed in response to electrostimulation to the His bundle or a bundle branch. In an example, the FFVA includes an EGM sensed via an electrode positioned within, or on the epicardial surface of, a ventricle. In an example as illustrated in the FIG. 1, the lead system may include a ventricular lead 107 including at least one RV electrode 131, which may be a tip electrode, a ring electrode, or a coil electrode. The His-bundle pacing system 118 may sense a FFVA signal (e.g., a far-field EGM) using the RV electrode 131 (e.g., as a cathode) and a reference electrode (e.g., as an anode). The EGM sensed as such using an RV electrode represents far-field LV activation, or far-field BiV activation. In an example, the reference electrode is a proximal electrode 132 on the ventricular lead 107. The proximal electrode 132 may be a coil electrode situated at the superior vena cava (SVC) of the heart. The distal electrode 131 and the proximal electrode 132 may also be used to deliver defibrillation shocks to correct ventricular tachyarrhythmia. In an example, the reference electrode may include the housing 116 or an electrode therein. In another example, the FFVA signal may be sensed using an atrial electrode 111 associated with the lead 106 and positioned in the RA and a reference electrode. In yet another example, the FFVA signal may be sensed using a His-bundle electrode associated with the lead 106 (e.g., electrode 112A or 112B) and a reference electrode. Examples of the reference electrode may include the housing 116 or an electrode therein. In another example, the FFVA signal may include a subcutaneous ECG signal sensed using subcutaneous chest electrodes such as located at the housing 116. In yet another example, the FFVA signal may include surface ECG signal sensed using skin electrodes attached to the body surface.

The His-bundle pacing system 118 may include electrostimulation circuitry configured to stimulate a patient physiologic conduction pathway (e.g., His bundle or a part of a bundle branch), restore cardiac synchrony, and therefore improve cardiac performance. The His-bundle pacing system 118 may include a control circuit to control the delivery of HBP according to patient atrioventricular (AV) conduction status, such as enabling HBP only if there is an indication of compromised AV conduction (e.g., various degrees of AV block). In some examples, the His-bundle pacing system 118 may additionally provide ventricular backup pacing (VBP) if the HBP does not capture the His-bundle and activate the ventricles. In the absence of AV conduction disturbance, or when the condition abnormality diminishes, the control circuit may control the electrostimulation circuitry to withhold delivery of HBP to promote patient intrinsic ventricular activation, and instead deliver bradycardia ventricular demand pacing (VDP). In some examples, the His-bundle pacing system 118 may distinguish between different types of AV conduction patterns, and adjust one or more of the HBP, VBP, or VDP configurations corresponding to the AV conduction patterns.

The IMD 104 may communicate with an external system 140 via a communication link 130. The external system 140 may include a dedicated hardware/software system such as a programmer, a remote server-based patient management system, or alternatively a system defined predominantly by software running on a standard personal computer. The external system 140 may include a proximal external device such as a programmer device in proximity of the IMD 104. A clinician may manage the patient 102 through the IMD 104 via the communication link 130. This may include, for example, programming the IMD 104 to sense physiological signals, analyzing the physiological signals to detect a medical condition such as heart failure, assessing therapy efficacy, performing a self-diagnostic test, or initiating or adjusting a therapy such as HBP. Additionally, the external system 140 may receive device data from the IMD 104 via the communication link 130. Examples of the device data may include real-time or stored physiological signals collected from the patient 102, physiological response to therapies delivered to the patient 102, or device operational status of the IMD 104 (e.g., battery status and lead impedance). The communication link 130 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

The external system 140 may monitor patient condition and the function of IMD 104. In various embodiments, the external system 140 may include a user interface to display received information to the user, and receive user input for operation control of the IMD 104. In an example, the external system 140 may be configured to verify pacing capture status, perform pacing threshold test to determine an HBP threshold. The capture verification and threshold testing may be executed periodically, or triggered by a specific event such as a user command. A user may use the external system 140 to program the IMD 104, such as to configure a pacing vector (e.g., specifying anode and cathode electrodes) to deliver HBP, or to configure a sense vector to sense a physiological signal.

The external system 140 may include a remote device in a location relatively distant from the IMD 104 and in communication with the proximal external device via a telecommunication network. The remote device may evaluate collected patient data and provide alert notifications, among other possible functions. In an example, the remote device may include a centralized server acting as a central hub for collected patient data storage and analysis. The server may be configured as a uni-, multi- or distributed computing and processing system. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the IMD 104. By way of example, alert notifications may include a Web page update, phone or pager call, E-mail, SMS, text or "Instant" message, as well as a message to the patient and a simultaneous direct notification to emergency services and to the clinician. Other alert notifications are possible. In various examples, the remote device may additionally include one or more locally configured clients or remote clients securely connected over the telecommunication network to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The external system 140 may output the detected medical events or therapy efficacy information (such as capture verification or classification) to a system user such as the patient or a clinician, or to a process including, for example, an instance of a computer program executable in a microprocessor. In an example, the process may include an automated generation of recommendations for initiating or titrating a medical therapy or an electrostimulation therapy. In an example, the external device 120 or the remote device 124 may include a respective display unit for displaying the physiological signals, stimulation parameters, capture verification, or AV conduction status, among other intermediate analyses and computations. Alerts, alarms, emergency calls, or other forms of warnings to signal the detected medical event may also be generated.

Portions of the IMD 104 or the external system 140 may be implemented using hardware, software, firmware, or combinations thereof. Portions of the IMD 104 or the external system 140 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
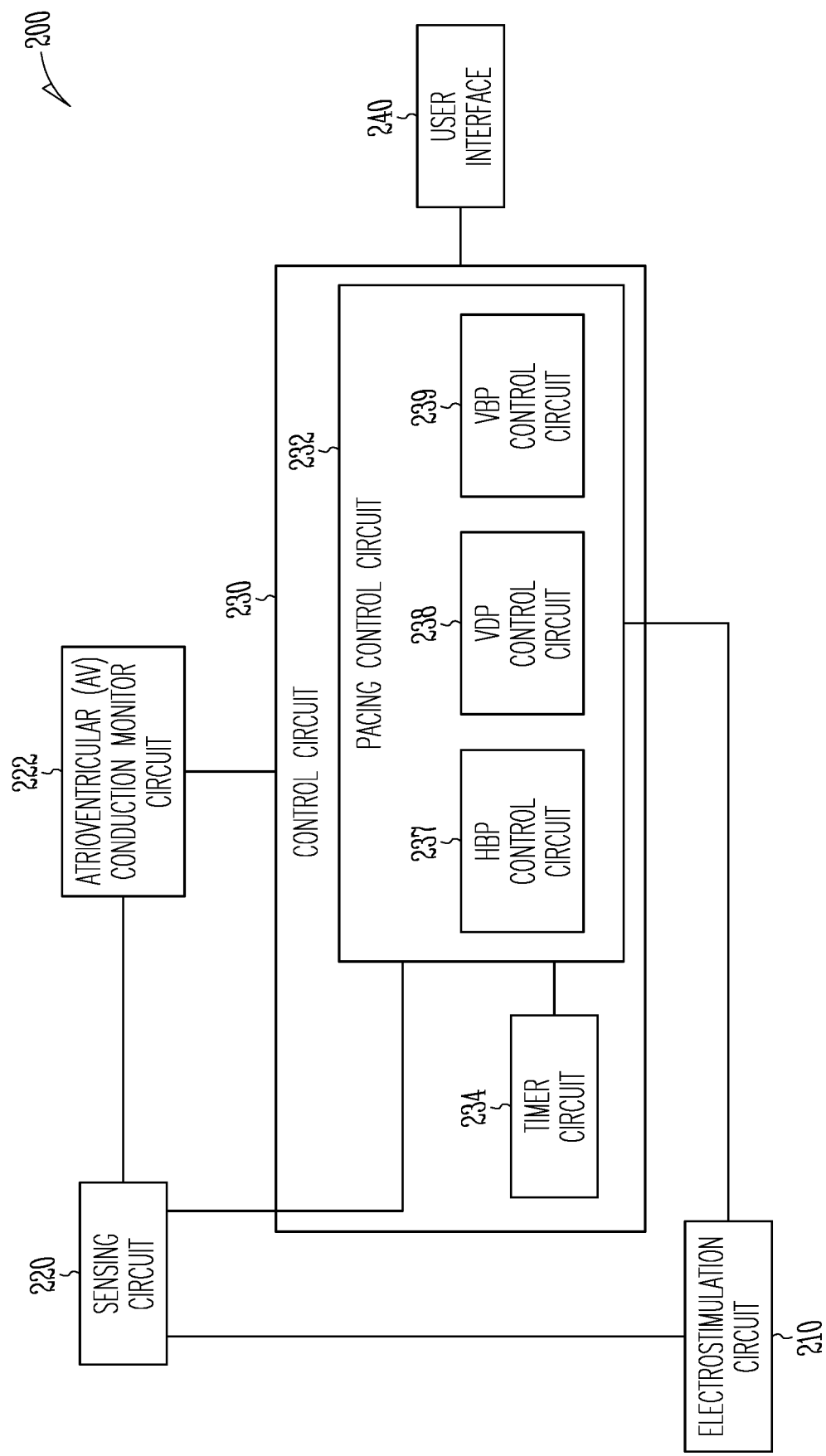
FIG. 2 is a block diagram illustrating an example of portions of a His-bundle pacing system.

FIG. 2 is a block diagram illustrating an embodiment of portions of a His-bundle pacing system 200. The His-bundle pacing system 200 represents an embodiment of the His-bundle pacing system 118, and may include an electrostimulation circuit 210, a sensing circuit 220, an atrioventricular (AV) conduction monitor circuit 222, a control circuit 230, and a user interface 240.

The electrostimulation circuit 210 may be configured to generate stimulation energy for delivery to the heart 102, such as via one or more leads and the associated electrodes. The electrostimulation circuit 210 may be configured to generate His-bundle pacing (HBP) pulses for delivery to a target pacing site at or near the His bundle or a bundle branch along the conduction pathway, such as via the lead 106 and one or more of the electrodes 112A-112B. The target site may include an interventricular septum region or a right atrial region near the His-bundle, or other conductive tissue on the physiologic conduction pathway, such as right or left bundle branches or fascicles, or Purkinje fibers. In an example, the HBP pulses may be delivered in multiple cardiac cycles, such that at least one pulse is delivered within each of the multiple cardiac cycles. In various examples, the electrostimulation circuit 210 may additionally generate electrostimulation to stimulate non-cardiac tissue, such as nerve tissue, muscle tissue, or other excitable tissue.

The electrostimulation circuit 210 may generate HBP pulses according to one or more stimulation parameters such as provided by control circuit 230. Examples of the stimulation parameters may include information about stimulation site, stimulation strength, stimulation mode, or stimulation timing, among other parameters. Stimulation site includes information about pacing site, pacing vector configuration (e.g., anode and cathode electrodes), unipolar or bipolar pacing, etc. Stimulation strength parameters determine the amount of energy delivered to the pacing site, and may include pulse amplitude, pulse width, pulse frequency, pulse waveform, duty cycle, or stimulation duration. In some examples, the stimulation parameters may include one or more HBP parameters such as pacing rate, pacing interval, or timing of HBP pulses, among others parameters, which are collectively referred to as HBP configuration in this document.

Stimulation mode includes, by way of example and not limitation, a His-bundle only mode, an atrial-Hisian (AH) pacing mode, a His-ventricular (HV) pacing mode, or an atrial-His-ventricular (AHV) pacing mode. In the His-bundle only pacing mode, atrial activation may be sensed by the His-bundle pacing electrode, such as by using a single pass lead, or a leadless pacemaker having a form factor with multiple electrodes positioned such that reliable atrial sensing may be achieved. In the AH pacing mode, the HBP pulses may be delivered only when intrinsic atrial activation (AS), or atrial pacing (AP), fails to produce propagatable depolarization of the AV node and the His bundle. The AH pacing mode may be suitable for patients with varying degrees of heart block or sick sinus syndrome. The HV pacing mode involves sequential pacing of the His bundle and the ventricle. The ventricular pacing may be provided in a demand mode, such that the ventricular pacing pulses are delivered only when the His pacing fails to produce propagatable depolarization of the ventricles. The HV pacing mode may be indicated for patients with persistent or chronic atrial fibrillation, or who have been treated with atrioventricular node ablation or drugs to slow and the rapid ventricular rhythm that often results and allow HBP to predominate. The AHV pacing mode involves sequential atrial, Hisian, and ventricular pacing. One or more of the His-bundle pacing or the ventricular pacing may be delivered in a demand mode. The AHV pacing mode may be indicated for patients with cardiac dyssynchrony and having received cardiac resynchronization therapy, patients suffering from HF with LBBB, HF induced by right ventricular pacing, long PR intervals with hemodynamic compromise, or pacemaker induced cardiomyopathy from conventional dual-chamber pacing.

Stimulation timing parameters determine the timing and sequence of pacing pulses. For example, in demand AH pacing mode, the HBP pulses are timed relative to an AS or an AP event. An AH timing represents a latency period, within a cardiac cycle, from an intrinsic AS event or an AP event to the delivery of an HBP pulse. In demand HV pacing mode, the ventricular pacing pulses are timed relative to a His pacing event. The HV timing represents a latency period, within a cardiac cycle, from a His bundle event (e.g., an HBP pulse) to the delivery of ventricular pacing pulse. In an example, if an HBP pulse fails to induce ventricular depolarization, a backup ventricular pacing may be delivered at the end of the HV timing.

The electrostimulation circuit 210 may be configured to provide selective pacing at a site with only a targeted tissue being directly excited, without substantial unintended and undesirable excitation of other non-targeted tissue. If the pacing directly causes intended excitation of the targeted tissue as well as unintended excitation of other non-targeted tissue, a non-selective pacing results. In the context of HBP, selective HBP causes only the excitation (depolarization) of the His bundle, without direct excitation of para-Hisian myocardium adjacent to the His bundle. Non-selective HBP directly causes excitation of both the His bundle and the para-Hisian myocardium. If the HBP pulses cause only excitation of the para-Hisian myocardium or other unintended cardiac tissue, without direct excitation of the His-bundle fibers, then a para-Hisian pacing results. If no tissue excitation is induced by HBP (e.g., neither the para-Hisian myocardium capture nor the His-bundle capture), then a complete loss of capture (LOC) results.

In addition to HBP, the electrostimulation circuit 210 may be configured to generate one or more of other pacing modalities, such as bradycardia ventricular demand pacing (VDP), cardiac resynchronization therapy (CRT), BiV pacing, or synchronized left ventricle (LV)-only pacing, single site pacing of only one site of a heart chamber (e.g., the left ventricle), or multisite pacing (MSP) of two or more sites of a heart chamber within the same cardiac cycle, among others. Similarly to HBP, these other pacing modalities may be delivered according to their respective stimulation strength, stimulation site, stimulation mode, or stimulation timing, among other parameters, such as provided by control circuit 230. In some examples, the electrostimulation circuit 210 may generate ventricular backup pacing (VBP) if HBP or other cardiac pacing modalities (e.g., VDP) do not capture the excitable tissue and activate the ventricles. The VBP pulses may be delivered to a target ventricular site via electrodes disposed on a ventricular lead. Additionally or alternatively, backup pacing may be delivered to the His bundle via electrodes on a His-bundle pacing lead.

In an example, VBP may include high-output pacing (HOP) pulses with higher pacing energy than conventional pacing pulses. The HOP pulse may be a biphasic or multiphasic waveform. In an example, the HOP pulse may have a peak-to-peak voltage amplitude of 5-8 volts, and a pulse duration of 50-70 msec. With higher amount of energy delivered to the myocardium, the HOP pulse may increase myocardial contractility and improve systolic function. However, chronic HOP pacing may overstress the heart and potentially be hazardous in some heart failure patients. According, in some examples, the HOP pulses may be delivered on an intermittent basis, such that the conventional pacing pulses are delivered in 3-5 cardiac cycles between the HOP pulses. In an example, the HOP pulses may be delivered when one or more physiologic sensors sense a deterioration in cardiac hemodynamics, in addition to the indication of loss of capture of para-Hisian capture. Arcot-Krishnamurthy et al. U.S. Pat. No. 8,588,907, entitled "CLOSED-LOOP CONTROL OF INTERMITTENT EXCITATORY CARDIAC STIMULATION FOR THERAPEUTIC EFFECT," refers to high-output pacing that is excitatory and of sufficient energy to augment myocardial contractility, which is incorporated herein by reference in its entirety.

The sensing circuit 220 may be coupled to one or more electrodes or physiologic sensors to sense a physiologic signal indicative of a response of a portion of the heart 102 to the delivery of HBP pulses. Examples of the sensed signals may include an electrocardiogram (ECG), an electrogram (EGM) of a portion of the heart such as atrial EGM, ventricular EGM, or evoked His potential, an impedance signal, a heart sound signal, or a pressure signal, among other physiological or hemodynamic signals indicative of a tissue response to the delivery of HBP pulses. In some examples, the sensing circuit 220 may sense a far-field ventricular activation (FFVA) signal. The FFVA signal may include a far-field electrical signal (e.g., an electrogram) indicative of electrical synchrony of depolarizations of the left and right ventricles in response to the HBP delivery. The far-field EGM may be sensed using a unipolar or a bipolar configuration. In an example, the far-field EGM may be sensed via a ventricular electrode positioned within or on the epicardial surface of an RV or LV, such as the distal electrode 131 on the ventricular lead 107 as shown in FIG. 1. In various examples, the far-field EGM may be sensed between the ventricular electrode 131 and the proximal electrode 132, between the ventricular electrode 131 and the housing 116 or an electrode therein, or between the ventricular electrode 131 and a joint electrode comprising the proximal electrode 132 and the housing 116 or an electrode therein that are at least temporarily electrically tied together. Such far-field EGMs sensed using the ventricular electrode 131 may represents far-field LV or far-field BiV (i.e., LV and RV) activations, as well as ventricular synchrony as manifested by QRS width or interventricular conduction delay. Additionally or alternatively, the FFVA signal may be sensed using electrodes positioned in or on other heart chambers or locations other than RV and LV. In an example, the FFVA signal may be sensed using an atrial electrode, such as the RA electrode 111 associated with the lead 106, and a reference electrode such as the housing 116 or an electrode therein. In yet another example, the FFVA signal may be sensed using electrodes positioned in or on a His-bundle region, such as one of the electrodes 112A-112B associated with the lead 106, and a reference electrode such as the housing 116 or an electrode therein. In yet another example, the FFVA signal may include a subcutaneous ECG signal sensed using chest electrodes such as located at the housing 116. Such FFVA signal may contain information about ventricular synchrony, such as QRS width or interventricular conduction delay. In some examples, the FFVA signal may include a mechanical signal indicative of mechanical synchrony of contractions and vibrations between of the left and right ventricles. Examples of the mechanical signal may include an impedance signal, a heart sound signal, a pressure signal, among other hemodynamic signals that may be sensed using a physiologic sensor.

The atrioventricular (AV) conduction monitor circuit 222 may be configured to detect an indication of presence or absence of AV conduction abnormality. During an AV conduction assessment session, HBP may be temporarily withheld, and the AV conduction monitor circuit 222 may measure, within a cardiac cycle, an AV conduction interval (AVI) between (1) an atrial sensed event (AS) or an atrial paced event (AP) and (2) a ventricular sensed event (VS). The AVI may be compared to an AVI threshold. The AV conduction is deemed abnormal if the AVI exceeds the AVI threshold (i.e., slow AV conduction), or the AV conduction is deemed normal if the AVI falls below said threshold. In an example, the AVI threshold is approximately 180 msec. In another example, the AVI threshold is approximately 200 msec.

In an example, the AV conduction monitor circuit 222 may detect AV conduction abnormality using RV to LV sense delay (RV-LV delay). Patients with conduction abnormality along the physiologic conduction pathway (e.g., bundle branch block) may present with desynchronized contractions between left and right ventricles. In an example, the AV conduction is deemed abnormal if the RV-LV delay exceeds a threshold, such as 60-80 msec. The AV conduction is deemed normal of the RV-LV delay falls below said threshold.

In an example, the AV conduction monitor circuit 222 may determine a QRS width from an ECG signal, a ventricular electrogram, or a FFVA signal as discussed above. The QRS width may be compared to a QRS width threshold. The AV conduction is deemed abnormal if the QRS width exceeds said threshold, or normal otherwise. An example of the QRS width threshold is approximately 80-120 msec. In another example, the QRS width threshold is approximately 150-200 msec. In some examples, statistics of multiple AVI measurements, or statistics of multiple QRS width measurements, may be used to provide a more robust assessment of AV conduction status. Examples of the statistics may include mean, median, mode, or other central tendency measures, or range, variability, or other second-order statistics.

In an example, the AV conduction monitor circuit 222 may detect AV conduction abnormality using a frequency of VDP delivery, represented by the amount of ventricular pacing delivered (e.g., number of pacing pulses, or time of pacing) within a specific time period. When a patient experiences AV conduction disturbance (e.g., slowed conduction), more VDP may be delivered. Therefore, by observing the frequency of VDP delivery, the presence or absence, and the degree of, AV conduction abnormality may be detected. In an example, the AV conduction is deemed abnormal if the VDP frequency exceeds a threshold, or normal otherwise.

The stimulation control circuit 232 may be configured to selectively activate or deactivate a pacing modality in accordance with the AV conduction status. In an example, the control circuit 230 may be implemented as a part of a microprocessor circuit in the cardiac disease management system 100. The microprocessor circuit may be a dedicated processor such as a digital signal processor, application specific integrated circuit (ASIC), microprocessor, or other type of processor for processing information including heart sounds. Alternatively, the microprocessor circuit may be a general-purpose processor that may receive and execute instructions of performing the functions, methods, or techniques described herein.

As illustrated in FIG. 2, the control circuit 230 may include circuit sets comprising a stimulation control circuit 232 and a timer circuit 234. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, movable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The AV conduction monitor circuit 222 may monitor AV conduction periodically at a specific frequency, and the control circuit 230 may activate or deactivate HBP delivery in accordance with the AV conduction status. In an example, if no AV conduction abnormality is present, then the stimulation control circuit 232 may control the electrostimulation circuit 210 to withhold delivery of HBP pulses. The stimulation control circuit 232 may further control the electrostimulation circuit 210 to enable bradycardia pacing of the ventricle (e.g., RV pacing via the electrode 131 and a reference electrode). The bradycardia pacing may be delivered in a ventricular demand mode (VDP), such that when no intrinsic ventricular activation is detected within an atrioventricular delay ($AVD_D$), then VDP pulses are delivered at the expiration of the $AVD_D$. The $AVD_D$ begins at the atrial sensed event (AS) or the atrial paced event (AP), and has a programmable duration.

If an indication of AV conduction abnormality is present, then the stimulation control circuit 232 may activate HBP, and the electrostimulation circuit 210 may stimulate the physiologic conduction pathway (e.g., His-bundle or a bundle branch). In some instances, the stimulation control circuit 232 may further control the electrostimulation circuit 210 to deliver ventricular backup pacing (VBP) if HBP fails to capture the physiologic conduction pathway and elicit ventricular activation. The VBP may be delivered at the expiration of a second atrioventricular delay $AVD_B$, if no ventricular activation is sensed during the $AVD_B$. The $AVD_B$ begins at an AS or AP event, and may have a programmable duration. In an example, the $AVD_B$ is approximately 150 msec. Alternatively, instead of timing the VBP with respect to an AS or AP event, the VBP may be delivered at a His-to-ventricular delay ($HVD_B$) with respect to HBP pulse. In an example, the $HVD_B$ is approximately 80 msec. In another example, the $HVD_B$ is approximately 70-100 msec.

The stimulation control circuit 232 may include one or more of an HBP control circuit 237, a VDP control circuit 238, or a VBP control circuit 239. These control circuits are configured to determine or adjust values of one or more stimulation parameters for the respective pacing modalities HBP, VDP, or VBP. Examples of the stimulation parameters may include pulse amplitude, pulse width, pulse rate, pulse shape or waveform, duty cycle, or stimulation duration, among others. Additionally or alternatively, one or more of the HBP control circuit 237, the VDP control circuit 238, or the VBP control circuit 239 may be configured to adjust a stimulation site for delivering respective pacing pulses, such as by switching to a different stimulation vector. For example, when HBP is activated in response to the detected AV conduction abnormality, the HBP control circuit 237 may determine or update an HBP parameter value, or adjust an HBP stimulation site. When VBP is activated to provide backup pacing in the event of non-captured HBP (e.g., LOC or para-Hisian capture), the VBP control circuit 239 may determine or update a VBP parameter value, or adjust a site for delivering backup pacing. Similarly, when VDP is activated in response to an absence of AV conduction abnormality, the VDP control circuit 238 may determine or adjust a VDP parameter, or switching to a different ventricular site to deliver the VDP pulses. Examples of adjustment of HBP and VBP in the event of AV conduction abnormality are discussed below, such as with reference to FIG. 3.

The timer circuit 234 may be configured to time the delivery of the stimulation pulses for the selected pacing modalities. In an example, the timer circuit 234 may time the delivery of HBP pulses using an atrio-Hisian delay (AHD). The AHD is a programmable time period with respect to an AS or an AP event. In an example, the AHD may be programmed to approximately 50 msec shorter than a sensed P wave-to-R wave (PR) interval or a programmed atrial-to-ventricular (AV) delay within a cardiac cycle. If an intrinsic His-bundle activity (Hs) is sensed within the AHD, the timer circuit 234 may initiate a His refractory period, during which an HBP pulse may be delivered. In another example, the AHD maybe determined based on an intrinsic AH interval, such that the AHD may be programmed to slightly longer than the intrinsic AH interval (e.g., approximately 1-30 msec longer than the intrinsic AH interval). The HBP would then be timed relative to an AS event but would occur just after the anticipated His event. In some examples, the delivery of the HBP pulse may trigger a His capture verification window during which a far-field ventricular activation (e.g., QRS), or a cardiac mechanical signal, may be sensed.

The timer circuit 234 may also time the delivery of ventricular backup pacing (VBP), such as by controlling the electrostimulation circuit 210 to deliver VBP pulses at the expiration of the atrioventricular delay ($AVD_B$) with respect to an AS or an AP event if no ventricular activation is detected within the $AVD_B$, or alternatively deliver VBP pulses at the expiration of the His-to-ventricular delay $HVD_B$ with respect to the HBP pulse delivery if no ventricular activation is detected within the $HVD_B$, as discussed above. In the event that HBP is withheld and bradycardia pacing VDP is activated, the time circuit 234 may time the delivery of VDP at the expiration of the atrioventricular delay $AVD_D$ if no ventricular activation is detected within the $AVD_D$, as discussed above. Examples of timing HBP or VBP pulses in the presence of AV conduction abnormality are discussed below, such as with reference to FIG. 3.

In some examples, the AV conduction monitor circuit 232 may distinguish between a sensed AV interval ($AVI_S$) and a paced AV interval ($AVI_P$). The $AVI_S$ represents an atrioventricular conduction delay from an AS event to a ventricular sensed (VS) event. The $AVI_P$ represents an atrioventricular conduction delay from an AP event to a VS event. If the $AVI_S$ exceeds a sensed AVI threshold, then the HBP control circuit 237 may control the electrostimulation circuit 210 to deliver the HBP pulses, such as at expiration of a sensed atrio-Hisian delay ($AHD_S$) that begins at the AS event. If the $AVI_S$ falls below sensed AVI threshold, then the HBP control circuit 237 may withhold delivery of the HBP pulses, and deliver ventricular demand pacing (VDP) at expiration of a sensed $AVD_D$ that begins at the AS event. In the case of AP event, if the $AVI_P$ exceeds a paced AVI threshold, then the HBP control circuit 237 may control the electrostimulation circuit 210 to deliver the HBP pulses, such as at expiration of a paced atrio-Hisian delay ($AHD_P$) that begins at the AP event. If the $AVI_P$ falls below paced AVI threshold, then the HBP control circuit 237 may withhold delivery of the HBP pulses, and instead deliver VDP at expiration of a paced $AVD_D$ that begins at the AP event.

In some examples, the AV conduction monitor circuit 232 may be configured to detect an AV block pattern. The pacing control circuit 232, or one or more of the sub-circuits (e.g., the HBP control circuit 237, the VDP control circuit 238, or the VBP control circuit 239), may control delivery of respective pacing modalities according to the detected AV block pattern. In an example, the AV conduction monitor circuit 232 may determine a target AV interval (AVI) using a plurality of AV intervals corresponding to conducted ventricular beats prior to a conduction block to the ventricle. Using the target AVI according to the type of the detected AV block pattern, the timer circuit 234 may determine an atrio-Hisian delay (AHD) and an atrio-ventricular delay ($AVD_B$). The electrostimulation circuit 210 to deliver the HBP pulses at the expiration of the determined AHD; and in the event of no HBP capture, to deliver the VBP pulses at the expiration of the determined $AVD_B$. Examples of the AV block pattern and using said pattern to control the HBP delivery are discussed below, such as with reference to FIG. 4.

The user interface 240 may include an input unit and an output unit. At least a portion of the user interface 240 may be implemented in the external system 140. The input unit may receive user input such as values of the parameters for physiologic event sensing, thresholds for AV conduction detection, thresholds for frequency of VBP delivery, and stimulation parameters for one or more pacing modalities such as HBP, VDP, or VBP, among others. The user input may receive user programming of stimulation parameters, or confirmation, rejection, or otherwise modification of the stimulation parameters generated by the pacing control circuit 232 or the timer circuit 234. The input unit may include an input device such as a keyboard, on-screen keyboard, mouse, trackball, touchpad, touch-screen, or other pointing or navigating devices.

The output unit may include circuitry configured to generate a human-perceptible notification of the AV conduction abnormality and the selected pacing modalities. The output unit may be coupled to a display for displaying the received physiologic signals (e.g., ECG, EGMs, FFVA signals, or cardiac mechanical activity signals), event sensing information such as atrial, ventricular, or His-bundle events, and timing information of the sensed events. The event sensing information may be overlaid with the signal tracings, or be displayed in a separate marker channel. The stimulation parameters, and intermediate measurements or computations may also be displayed. The output unit may be coupled to a printer for printing hard copies of information about the event detection and therapy titration protocol. The information may be presented in a table, a chart, a diagram, or any other types of textual, tabular, or graphical presentation formats. The presentation of the output information may include audio or other media formats. In an example, the output unit may generate alerts, alarms, emergency calls, or other forms of warnings to signal the system user about the His-bundle capture status, AV conduction status, change of pacing modalities, or adjustment of stimulation parameters. In an example, the output unit may generate an alert when a loss of capture is indicated and VBP is delivered. In another example, frequent VBP may trigger the output unit to generate an alert and prompt a user (e.g., a clinician) to reprogram the pacing system.

Portions of the His-bundle pacing system 200 may be implemented distributedly between two devices. In an example, a first device may include the electrostimulation circuit 210 and a stimulation delivery system such as the lead and associated electrodes for delivering the HBP pulses, and a second device may include the sensing circuit 220 and at least a portion of the control circuit 230. The sensing circuit 220 of the second device may be configured to sense, among other signals, the far-field ventricular response to the HBP pulses. In an example, the first and second devices are both implantable devices. In another example, at least one of the first or the second device is a non-implantable, wearable device.

Figure 3:
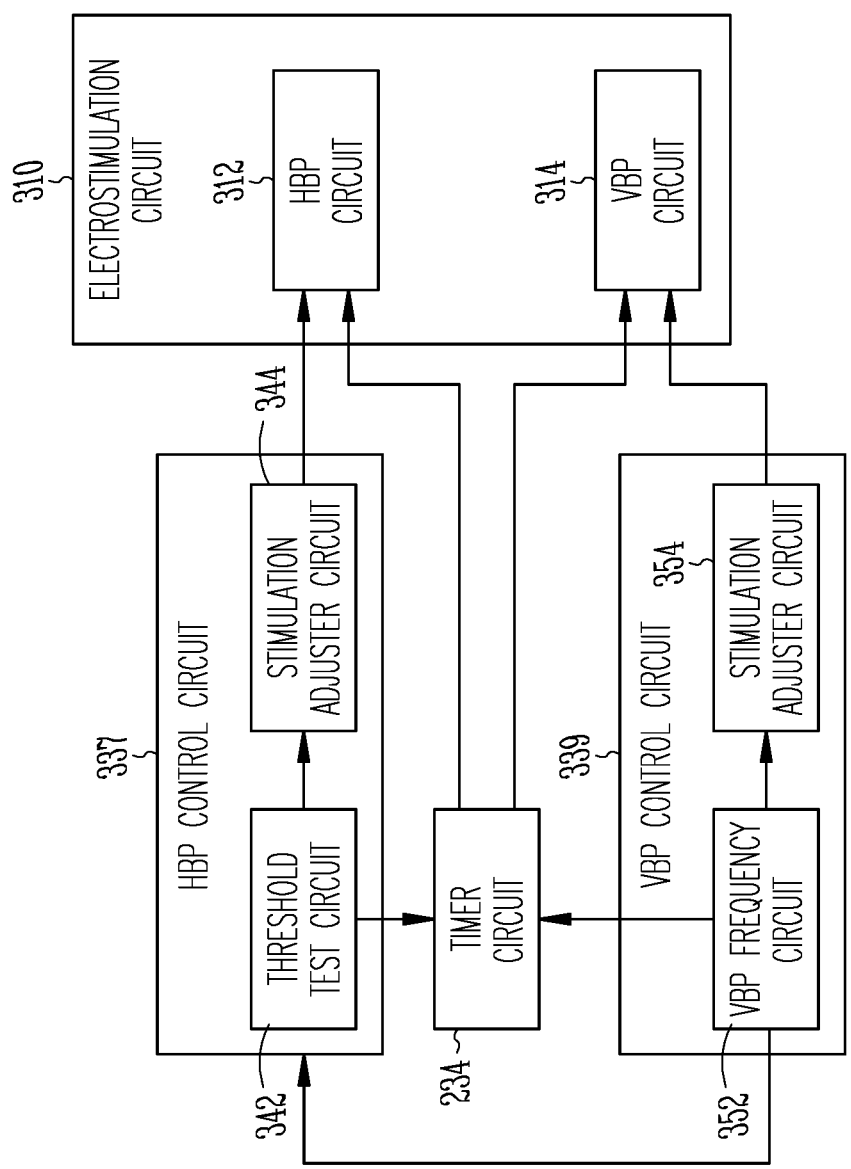
FIG. 3 is a block diagram illustrating an example of portions of an HBP system that may deliver HBP and VBP in the presence of AV conduction abnormality.

FIG. 3 is a block diagram illustrating generally an example of portions of an HBP system 300 configured to deliver HBP and VBP in the presence of AV conduction abnormality. The illustrated system portion 300 may be a part of the His-bundle pacing system 200, and includes an HBP control circuit 337, a VBP adjuster circuit 339, a timer circuit 234, and an electrostimulation circuit 310.

The HBP control circuit 337, which is an embodiment of the HBP control circuit 237, may include a threshold test circuit 342 and a stimulation adjuster circuit 344. The threshold test circuit 342 may be configured to test the HBP threshold, which represents minimal energy required to produce His-bundle capture. The HBP threshold may change over time, such as due to changes in patient pathophysiology, medication, or lead migration or dislodgment. To maintain the desired capture status, the HBP threshold test may be carried out periodically, or triggered by a specific event, such as when HBP pulses fail to capture the His bundle but instead consistently produce para-Hisian capture or LOC, or by a user command.

The HBP threshold test may involve delivering HBP pulses to a His bundle or other portion of the physiologic conduction pathway in accordance with a threshold test protocol, such as using the electrostimulation circuit 210. HBP pulses may be delivered at a rate 10-20 bpm above the measured atrial rate. The threshold test protocol may be machine-readable instructions stored in a memory device, and executable by a machine such as a microprocessor. The instructions specify programming a stimulation parameter to different values and measuring, for each programmed parameter value, a corresponding capture status. In various examples, the stimulation parameter, such as pulse amplitude, may be incremented following a ramp-up protocol, decremented following a ramp-down protocol, or sweep through a set of parameter values such as stored in a storage device. For each stimulation parameter value (e.g., pulse amplitude), the HBP control circuit 337 determines a His-bundle capture status. In an example, the capture status may be determined using QRS width measured from a ventricular EGM, or a FFVA signal. As the stimulation parameter value is changed such as according to the threshold test protocol, the HBP control circuit 337 may detect a transition from a first capture status to a second capture status of a different type, and determine an HBP threshold based on that detected transition of capture status. In an example, the HBP control circuit 337 may generate a QRS width trend corresponding to multiple descending stimulation strength values in a ramp-down protocol, detect from the QRS width trend prolongation of QRS width exceeding a threshold, and determine the HBP threshold using the stimulation strength value corresponding to the detected prolongation of QRS width. In another example, the QRS width trend may correspond to multiple ascending stimulation strength values in a ramp-up protocol. The HBP control circuit 337 may detect from the QRS width trend a shortening of QRS width falling below a threshold, and determine the HBP threshold using the stimulation strength value corresponding to the detected shortening of QRS width. In some examples, the His-bundle capture status may be determined using morphology of a QRS complex in a ventricular EGM or a FFVA signal. For example, a similarity metric between a QRS morphology and a morphology template represented by morphological features of the same EGM vector corresponding to His-bundle capture and cardiac synchrony, and decides His-bundle capture if the similarity metrics satisfies a specified condition. In some examples, to improve reliability of His-bundle capture status decision, capture verification may be performed for a plurality of HBP pulses delivered over a number of cardiac cycles. A His-bundle capture (e.g., selective or non-selective His bundle capture) is determined to have occurred if a substantial amount (e.g., more than 50%) of the plurality of HBP pulses result in individual His-bundle captures.

The stimulation adjuster circuit 344 may determine or update an HBP stimulation parameter using the HBP threshold determined by the threshold test. In an example, the stimulation adjuster circuit 344 may set the HBP pulse amplitude to the HBP threshold plus a safety margin. One or more other stimulation parameters, such as pulse width, pulse rate, pulse waveform, duty cycle, or stimulation duration, may also be adjusted to more effectively capture the His-Purkinje system.

The stimulation adjuster circuit 344 may additionally adjust a stimulation site for HBP, such as switching to a different stimulation vector to deliver the HBP pulses, if the HBP under the present configuration fails to capture the His bundle or the conduction pathway, or if the HBP threshold has changed from previous threshold. The stimulation vector may include an HBP electrode more distal than the existing electrode for delivering HBP pulses. Effective propagation of the action potentials through the His-Purkinje system to restore cardiac synchrony may be achieved if the HBP pulses are delivered distal to the blockage site. HBP pulses delivered proximal to the blockage site (i.e., above the blockage site), even if capable of activating the proximal portion of the His bundle, cannot cause the action potentials to propagate to the ventricles through the His-Purkinje system and produce synchronized ventricular contractions. In the event of no His-bundle capture is indicated at a first His bundle site (e.g., para-Hisian myocardium capture, or LOC), or if the HBP threshold has changed from the existing pacing threshold, the stimulation adjuster circuit 344 may reconfigure the HBP pacing vector to deliver HBP pulses from a second His bundle site more distal than the first His bundle site, or to deliver HBP pulses from a bundle branch site (e.g., a left bundle branch site). In an example, the stimulation adjuster circuit 344 may adjust stimulation site if a specified number of attempts of pacing parameter adjustment (e.g., HBP pulse amplitude, pulse width, pulse rate, or pulse shape) still fail to restore ventricular synchrony.

The VBP control circuit 339, which is an embodiment of the VBP control circuit 239, may include a VBP frequency circuit 352 and a stimulation adjuster circuit 354. The VBP frequency circuit 352 may determine an indication of VBP delivery frequency. As VBP may be delivered as backup in the event of non-captured HBP, highly frequent VBP delivery may indicate less effective HBP therapy to capture the physiologic conduction pathway and restore cardiac synchrony. The VBP frequency circuit 352 may determine a count or time of VBP pulses being delivered within a specific time period. If said count or time exceeds a threshold value, then VBP is deemed frequent. The stimulation adjuster circuit 354 may adjust one or more stimulation parameters (e.g., pulse amplitude, pulse width, pulse rate, or pulse waveform, duty cycle, stimulation duration, etc.), and/or stimulation site. Additionally or alternatively, frequent VBP delivery (e.g., VBP count or time exceeding a threshold) may trigger the HBP control circuit 337 to initiate HBP configuration optimization, such as running an HBP threshold test, adjusting one or more HBP stimulation parameters, or changing HBP stimulation site (e.g., switch to another HBP pacing vector).

If the VBP frequency circuit 352 detects that the VBP count or time falls below the threshold value, then VBP is deemed infrequent. This may suggest that the present HBP configuration is acceptable and no adjustment is necessary. The HBP and VBP may be delivered under the existing parameter setting and timing schedule. Alternatively, the AV conduction status may be reevaluated, such as via the conduction monitor circuit 222. The AV conduction reevaluation may be carried out on a periodic basis (e.g., every specific number of cardiac cycles, or a specific time period such as specific number of hours, days, or weeks), or triggered by a user (e.g., by a clinician during an office visit or device follow-up). During the reevaluation, HBP may be temporarily disabled. Intrinsic or atrial paced AV interval (AVI, measured between an AS or an AP event and the resultant VS event) may be measured. If the measured AVI is within an acceptable range indicating no signs of AV condition abnormality (e.g., AVI falls below a threshold, such as 180 msec), then the HBP control circuit 337 may control the HBP circuit 312 to withhold HBP delivery, and the VDP control circuit 238 may control the HBP circuit 312 to deliver bradycardia pacing VDP. However, if the measured AVI indicates that AV condition abnormality persists (e.g., AVI exceeds a threshold, such as 180 msec), then HBP and VBP with respective existing parameter settings and timing schedules may be delivered. As an alternative to the AVI, the reevaluation of AV conduction status may involve QRS width or morphology taken from ventricular EGM or a FFVA signal, as discussed above. Periodic reevaluation of AV conduction status may help promote intrinsic AV conduction and reduce the HBP, in cases the AV conduction disturbance diminishes or becomes absent.

The timer circuit 234 may time the delivery of HBP pulses and VBP pulses. As illustrated in FIG. 3, the timer circuit 234 may determine the timing of HBP pulses or the VBP pulses using the HBP threshold test information and the VBP frequency information. For example, the highly frequent VBP delivery may trigger the timer circuit 234 to adjust timing for delivering HBP pulses (e.g., AHD) or timing for delivering VBP pulses (e.g., $AVD_B$ or $HVD_B$). In an example, the timer circuit 234 may extend $AVD_B$ to increase the chance for the HBP pulses to conduct and activate the ventricles. This may be beneficial in those cases where the HBP pulses capture the His-bundle but the conduction to the ventricle are slowed due to functional delays along the conduction pathway. Extending the $AVD_B$ may increase the effectiveness of HBP and promote the use of physiologic conduction pathway, and avoiding long-term harmful hemodynamic effects associated with excessive ventricular pacing via VBP.

In some examples, in response to a detection of frequency VBP delivery (e.g., VBP count or time exceeding a threshold), the HBP control circuit 337 may assess HBP capture status. If non-capture (e.g. LOC or para-Hisian myocardium capture) is indicated, then the threshold test circuit 342 may perform an HBP threshold test, and the HBP control circuit 337 may optimize one or more HBP stimulation parameters accordingly. If, however, the HBP with present parameter setting successfully capture the His bundle or the conduction pathway (e.g., a selective or non-selective His bundle capture), then the excessive VBP is more likely due to inappropriately short $AVD_B$. The timer circuit 234 may extend the $AVD_B$ to increase the chance for the HBP pulses to conduct and activate the ventricles.

The electrostimulation circuit 310, which is an embodiment of the electrostimulation circuit 210, may include an HBP circuit 312 and a VBP circuit 314. In the presence of the AV conduction abnormality, the HBP circuit 312 may deliver HBP in accordance with the adjusted stimulation parameters and/or sites provided by the HBP control circuit 337 and the timing of HBP pulses provided by the timer circuit 234. If the HBP fails to capture the His bundle and activate the ventricles, the VBP circuit 314 may deliver VBP pulses in accordance with the adjusted stimulation parameters and/or sites provided by the VBP control circuit 339 and the timing of VBP pulses provided by the timer circuit 234.

Figure 4:
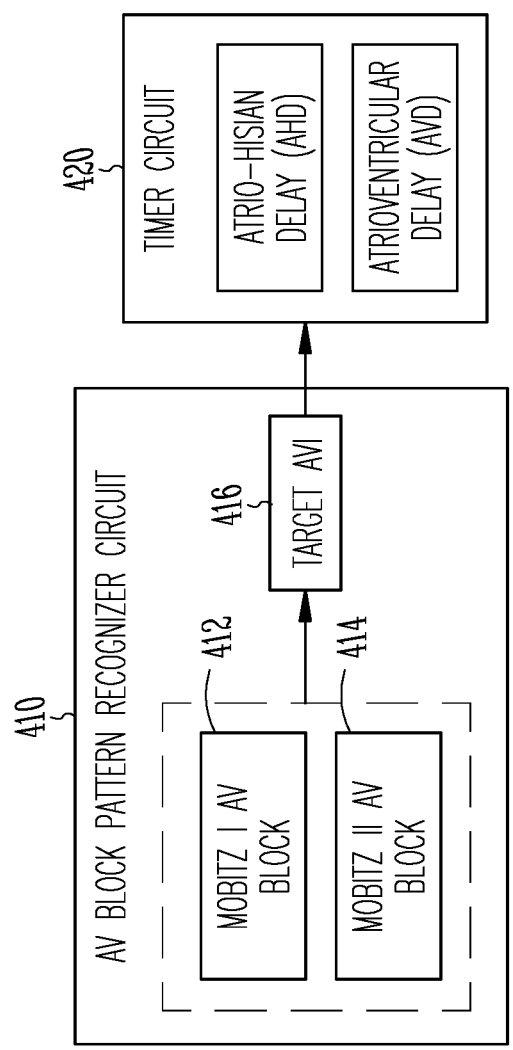
FIG. 4 is a block diagram illustrating an example of portions of an HBP system that time the delivery of HBP and VBP based on an AV block pattern.

FIG. 4 is a block diagram illustrating an example of portions of an HBP system 400 configured to time the delivery of HBP and VBP using an AV block pattern. The system portion 400 may be a part of the His-bundle pacing system 200, and includes an AV block pattern recognizer circuit 410 and a timer circuit 420. The AV block pattern recognizer circuit 410 may recognize an AV block pattern, such as one of a first-degree AV block (represented by PR prolongation), a second-degree AV block, or a third-degree AV block (represented by complete AV dissociation). In some examples, the AV block pattern recognizer circuit 410 may recognize a type of the second-degree AV block, such as a Mobitz type I bock (also known as Wenckebach block) 412 or a Mobitz type II block 414. Mobitz type I block 412 is usually a reversible block of the AV node. When the AV node is severely blocked, it fails to conduct an impulse. Mobitz I is a progressive failure, and usually associated with a low risk of heart attack. Mobitz II may be related to a failure of the His-Purkinje cells responsible for the rapid propagation in the heart. Mobitz II may be caused by a sudden and unexpected failure of the His-Purkinje cells, and may lead to severe heart attack.

The AV block pattern recognizer circuit 410 may initiate a test to determine AV block types periodically at a specific time period, such as every 21 hours. In an example, the test may last for 5 to 10 minutes, during which the AV intervals are monitored. The recognition of AV block pattern may be based on AV intervals corresponding to conducted ventricular beats prior to a conduction block to the ventricle. In an example, the AV block pattern recognizer circuit 410 may recognize AV block pattern using an AV interval trend over a plurality of AV intervals. In another example, the AV block pattern recognizer circuit 410 may recognize AV block pattern using an AV interval statistic, such as an average or other central tendency measures, or variability or other second-order statistics, of a plurality of AV intervals. In an example, the AV block pattern recognizer circuit 410 may recognize a first-degree AV block if the trended AV interval, or a central tendency of the AV intervals, exceeds a threshold, such as approximately 200 msec in an example.

As illustrated in FIG. 4, the AV block pattern recognizer circuit 410 may recognize Mobitz I block 412 based on an AV interval pattern characterized by progressive prolongation of AV intervals on consecutive beats followed by a blocked AS event, or recognize Mobitz II block 414 by based on an AV interval pattern characterized by intermittently non-conducted atrial events, not preceded by AV prolongation and not followed by AV shortening. There is usually a fixed number of non-conducted atrial events for every successfully conducted QRS complex.

The AV block pattern recognizer circuit 410 may determine a target AV interval (AVI) 416 using a plurality of AV intervals corresponding to conducted ventricular beats prior to a conduction block to the ventricle. The target AVI 416 is a representative AVI for the recognized AV conduction pattern, such as Mobitz type I or Mobitz type II block. The target AVI 416 may be individually and separately determined for the recognized AV conduction pattern. In an example, for a recognized Mobitz type I block 412, the target AVI 416 may be a shortest interval ($AVI_{min}$) among a plurality of progressively prolonged AV intervals prior to the conduction block to the ventricle. In another example, for a recognized Mobitz type II block 414, the target AVI 416 may be an average ($AVI_{avg}$) or other central tendency of the plurality of conducted AV intervals prior to a conduction block.

The timer circuit 420 is an embodiment of the timer circuit 234, and may be configured to determine timing for delivering pacing pulses of a selected pacing modality, such as HBP or VBP in the presence of AV conduction abnormality. The timer circuit 420 may determine an atrio-Hisian delay (AHD) for delivering HBP using the target AVI. The electrostimulation circuit 210 may deliver the HBP pulses at expiration of the determined AHD. In an example, the AHD may be determined using a difference between the target AVI and a His-to-ventricular interval (HVI), that is:

$$AHD = AVI - HVI + \Delta 1 \qquad (1)$$

where $\Delta 1$ is a user-programmable offset. In an example, $\Delta 1$ may be approximately 10 msec. The offset $\Delta 1$ allows the intrinsic or atrial paced impulses (AS or AP) to conduct through the His-bundle and the conduction pathway, while the HBP would not compete with the AS or AP events as it is still in the refractory period. The offset $\Delta 1$ also allows for His-bundle capture if the AS or AP events are blocked, thereby still maintaining consistent AV conduction. The HVI may be estimated during a test where HBP is delivered and the resultant ventricular response is detected. In the event that the AV block is a Mobitz type I block, the AHD may be determined to be $AVI_{min} - HVI + \Delta 1$. Similarly, for Mobitz type II block, the AHD may be determined to be $AVI_{avg} - HVI + \Delta 1$.

In some instances, it is desirable to time the delivery of HBP such that that the ventricular activation is caused by HBP rather than AS or AP events. The AHD may be set to just shorter than sensed atrio-to-Hisian (AHI) interval between an AS or an AP event to the resultant His bundle activation. An AHD that is shorter than the sensed AHI may help avoid fusion or competition between HBP pulse and the activation wavefront conducted from the atrium due to an AS or an AP event, and may increase the chance that HBP takes control over the conducted AS or AP events to activate the ventricles.

Mobitz type I block usually occurs in regular cycles, and may have a fixed ratio between the number of atrial events (P waves) and the number of QRS complexes per cycle. In some patients, Mobitz type II block may also occur with a fixed P to QRS ratio, with a set number of P waves for every successfully elicited QRS. This ratio is also frequently specified in referring to 3:1, 4:1, 5:1, or higher Mobitz type II block. In an example, the timer circuit 420 may monitor the AV conduction pattern over a period of time, and determine presence of a relatively consistent P to QRS ratio. Based on the P to QRS ratio, the timer circuit 420 may predict when the next P wave will drop, and determine the AHD to be just prior to the P wave. This allows the HBP to be delivered only at the time that P wave is dropped (not conducted through), and promotes the intrinsic AV conduction prior to the dropped P wave.

In some examples, when a Mobitz type II block 414 is recognized, the AV block pattern recognizer circuit 410 may determine a statistic of conducted beats prior to a conduction block to the ventricle. By way of example, the statistic of conducted beats includes an average number (or other central tendency) of conducted beats before a block occurs during Mobitz type II block. The timer circuit 420 may use this statistic to determine the timing and manner of HBP delivery, such as intermittent delivery of HBP pulses. For example, the timer circuit 420 may control the electrostimulation circuit 210 to deliver HBP pulses for a first number (M) of consecutive cardiac cycles, followed by withholding the HBP delivery for a second number (N) of cardiac cycles. During the withholding of HBP, intrinsic AV conductions are allowed to happen and to activate the ventricles. The first number M may correspond to the average number of non-conducted beats or those beats with significant AV conduction disturbance (e.g., long AV intervals). Delivering the HBP for M cardiac cycles during which block or substantial AV conduction disturbance may occur may improve cardiac function. The second number N may correspond to the average number of conducted beats with no significant AV conduction disturbance (e.g., short AV intervals), such that the withholding of HBP may promote intrinsic conduction and ventricular activation.

The timer circuit 420 may determine an atrioventricular interval ($AVD_B$) for ventricular backup pacing (VBP) using the target AVI. In an example, the $AVD_B$ may be determined using as a sum of the target AVI and an offset 42, as represented in the following:

$$AVD_B = AVI + \Delta 2 \qquad (2)$$

The offset Δ2 may be a programmable value. In an example, the offset Δ2 is approximately 20-30 msec if HBP is active. In the case that HBP is disabled (e.g., by the user or automatically disabled), VBP may provide backup pacing in case the intrinsic or paced beats from the atrium (e.g., AS or AP events) do not conduct and activate the ventricles. Then a longer Δ2 may be used to promote intrinsic conduction. In an example, Δ2 may be approximately 80 msec. The electrostimulation circuit 210 may deliver VBP at expiration of the $AVD_B$, if no ventricular activation is sensed during the $AVD_B$.

Figure 5:
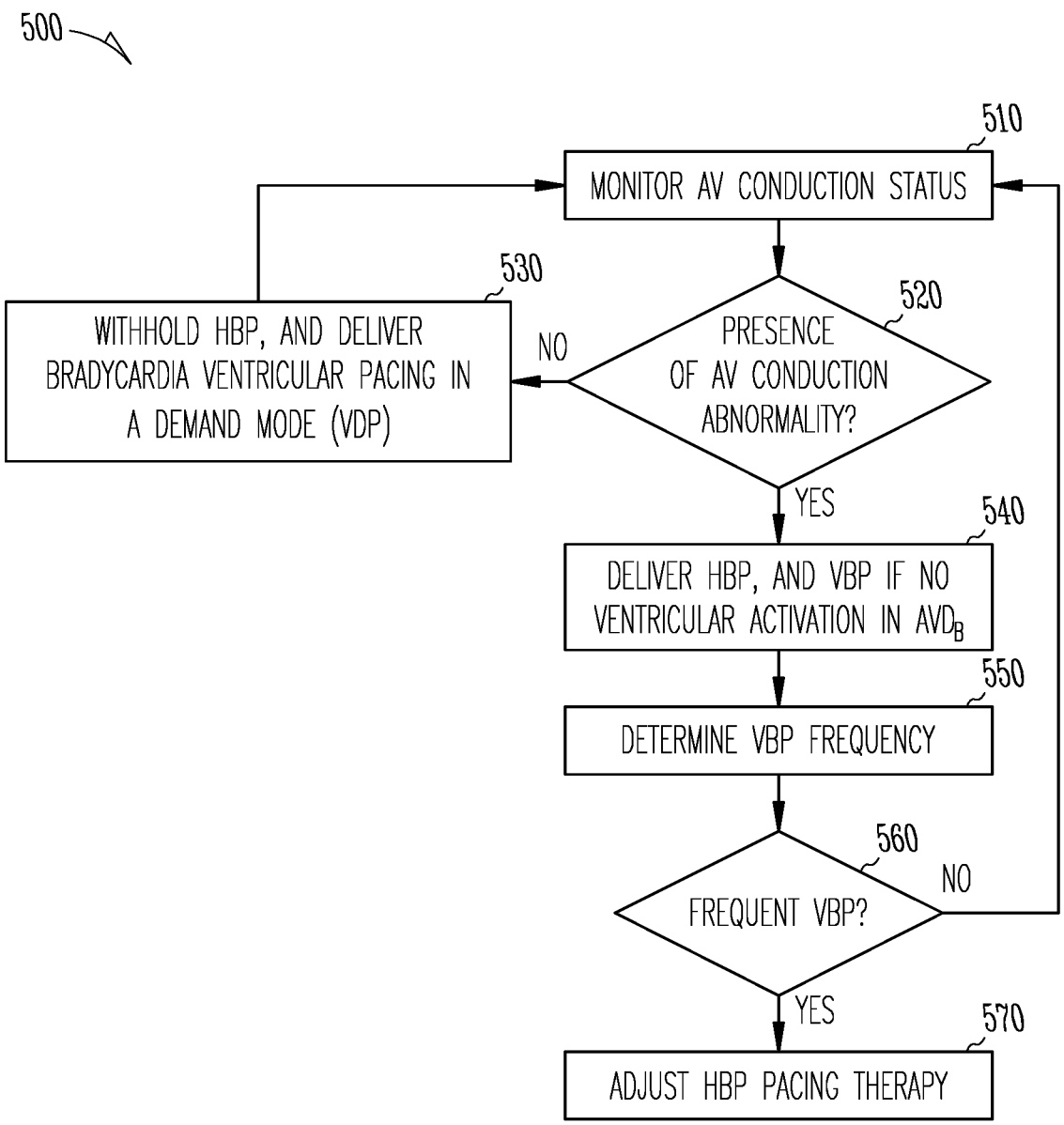
FIG. 5 is a flowchart illustrating generally an example of a method for dynamic control of HBP using a medical system.

FIG. 5 is a flowchart illustrating generally an example of a method 500 for providing His-bundle pacing (HBP) to a patient using a medical system. In particular, the method 500 may be used dynamically control HBP delivery (e.g., initiation or withholding of the HBP, and timing of the HBP delivery) based on patient AV conduction status. The method 500 may be implemented in and executed by an ambulatory medical device such as an implantable or wearable medical device, or in a remote patient management system. In an example, the method 500 may be implemented in, and executed by, the IMD 104, one or more devices in the external system 140, or the His-bundle pacing system 200.

The method 500 commences at 510, where patient AV conduction status may be monitored continuously or periodically to determine if an indication of AV conduction abnormality is present, such as using the conduction monitor circuit 222. In an example of periodic assessment of AV conduction status, HBP may be temporarily withheld, and bradycardia ventricular pacing may be delivered in a demand mode (VDP), such as a VVI or DDD bradycardia pacing mode where ventricular pacing may be delivered when no intrinsic ventricular activation is detected within an atrioventricular delay.

At 520, presence or absence of an indication of AV conduction abnormality may be detected. In an example, the AV conduction abnormality may be detected using an AV conduction interval (AVI) from atrial sensed event (AS) or an atrial paced event (AP) to a ventricular sensed event (VS). The AV conduction is deemed abnormal if the AVI exceeds the AVI threshold (e.g., approximately 180 msec), otherwise the AV conduction is deemed normal or acceptable. Alternatively, the AV conduction status may be detected using a QRS width measured from an ECG signal, a ventricular electrogram, or a FFVA signal. The AV conduction is deemed abnormal if the QRS width exceeds a QRS width threshold (e.g., approximately 80-120 msec), otherwise the AV conduction is deemed normal or acceptable. Alternatively, the AV conduction abnormality may be detected using a frequency of VDP delivery. For example, an abnormal AV conduction is detected if the VDP frequency exceeds a threshold.

If no indication of AV conduction abnormality is detected at 520, then at 530, the HBP may be withheld (if it has been actively delivered prior to the AV conduction status assessment). Withholding HBP and promoting patient intrinsic cardiac conduction during normal AV conduction may not only avoid any unnecessary therapies (e.g., HBP or ventricular pacing), but may bring about more favorable ventricular performance and hemodynamic outcome. It may also help reduce pacing time and pacing energy associated with HBP, conserve battery power, and extend implantable device longevity. Along with the inhibited HBP, in some examples, bradycardia ventricular pacing therapy (VDP) may be delivered in a demand mode, such that VDP pulses may be delivered upon the expiration of a first atrioventricular delay ($AVD_D$) if no intrinsic ventricular activation is sensed during the $AVD_D$. The $AVD_D$ begins at the atrial sensed event (AS) or the atrial paced event (AP), and has a programmable duration. A long AVD, such as between 200-250 msec in a non-limiting example, may be programmed to promote intrinsic ventricular activation.

If AV conduction abnormality is detected at 520, then at 540, the HBP may be activated, and stimulation pulses be delivered to the physiologic conduction pathway (e.g., His-bundle or a bundle branch). The HBP pulses may be delivered in accordance with stimulation waveform parameters, stimulation site, stimulation timing, among others. In an example, at 540, the HBP waveform parameters and/or stimulation site may be programmed or adjusted by a user, or automatically determined or adjusted such as by the HBP control circuit 237. The stimulation timing (for delivering HBP pulses) may be automatically controlled by the timer circuit 234. In an example, HBP pulses may be delivered following an atrio-Hisian delay (AHD) an intrinsic (AS) or paced atrial event (AP).

The delivery of the HBP pulse may trigger His capture verification using a ventricular electrical or mechanical signal or a FFVA signal. If HBP fails to capture the physiologic conduction pathway and elicit ventricular activation, ventricular backup pacing (VBP) may be delivered at the expiration of a second atrioventricular delay $AVD_B$ if no ventricular activation is sensed during the $AVD_B$. The $AVD_B$ begins at an AS or an AP event, and may have a programmable duration, such as approximately 150 msec in a non-limiting example. Alternatively, VBP may be delivered at a His-to-ventricular delay $HVD_B$ with respect to HBP pulse. Stimulation parameters for the VBP, including waveform parameters and/or stimulation site, may be programmed or adjusted by a user, or automatically determined or adjusted such as by the VBP control circuit 239. The stimulation timing (for delivering VBP pulses), such as the $AVD_B$ or $HVD_B$, may be automatically controlled by the timer circuit 234. Examples of methods of timing the HBP or VBP in the presence of AV conduction abnormality are discussed below, such as with reference to FIG. 6.

In some examples, the AV conduction status may be detected separately and respectively for an atrial sensed event (AS) and for an atrial paced event (AP). An atrioventricular conduction interval $AVI_S$ may be measured from an AS event to a ventricular sensed (VS) event. At 520, if the $AVI_S$ falls below a sensed AVI threshold, then at 530, HBP may be withheld for subsequent AS events. Bradycardia ventricular pacing (VDP) may be delivered at expiration of a sensed AVD that begins at the AS event. However, if the $AVI_S$ exceeds the sensed AVI threshold, then at 540 HBP may be delivered at expiration of a sensed atrio-Hisian delay $(AHD_S)$ that begins at the AS event. If HBP fails to capture and elicit ventricular activation, VBP may be delivered at the expiration of a second atrioventricular delay $AVD_B$ that begins at the AS event.

Similarly, for an AP event, an atrioventricular conduction interval $AVI_P$ may be measured from the AP event to a VS event. At 520, if the $AVI_P$ falls below a paced AVI threshold, then at 530, HBP may be withheld for subsequent AP events. VDP may be delivered at expiration of a paced AVD that begins at the AP event. However, if the $AVI_P$ exceeds the paced AVI threshold, then at 540 HBP may be delivered at expiration of a paced atrio-Hisian delay $(AHD_P)$ that begins at the AP event. If HBP fails to capture and elicit ventricular activation, VBP may be delivered at the expiration of a second atrioventricular delay $AVD_B$ that begins at the AP event.

At 550, a VBP delivery frequency may be determined such as on a periodic basis when the HBP and VBP are delivered in the presence of AV conduction abnormality. The VBP frequency may be represented by a count or time of VBP pulses being delivered within a specific time period. At 560, the VBP frequency may be compared to a threshold to determine if too many VBP is delivered within the specific time period. If the VBP frequency falls below the threshold, then the VBP is deemed infrequent, and the HBP and VBP with the existing parameter setting and timing schedule may be continued at 540. Alternatively, the AV conduction status may be reevaluated at 510. The reevaluation of AV conduction status may be performed on a periodic basis (e.g., every specific number of cardiac cycles, or a specific time period such as specific number of hours, days, or weeks), or triggered by a user (e.g., by a clinician during an office visit or device follow-up).

If at 560 the VBP frequency exceeds a threshold value, then VBP is deemed frequent. Then at 570, the HBP therapy may be adjusted to optimize its efficacy. For example, one or more stimulation parameters (e.g., pulse amplitude, pulse width, pulse rate, or pulse waveform, duty cycle, stimulation duration, etc.), and/or stimulation site, may be adjusted. In an example, HBP capture status may be evaluated following the HBP delivery at 540. If non-capture (e.g. LOC or para-Hisian myocardium capture) is indicated, then a HBP threshold test may be performed at 570, and one or more HBP stimulation parameters may be adjusted based on the HBP threshold. If HBP with present parameter setting successfully capture the His bundle or the conduction pathway (e.g., a selective or non-selective His bundle capture), then the $AVD_B$ may be extended to increase the chance for the HBP pulses to conduct and activate the ventricles.

Figure 6:
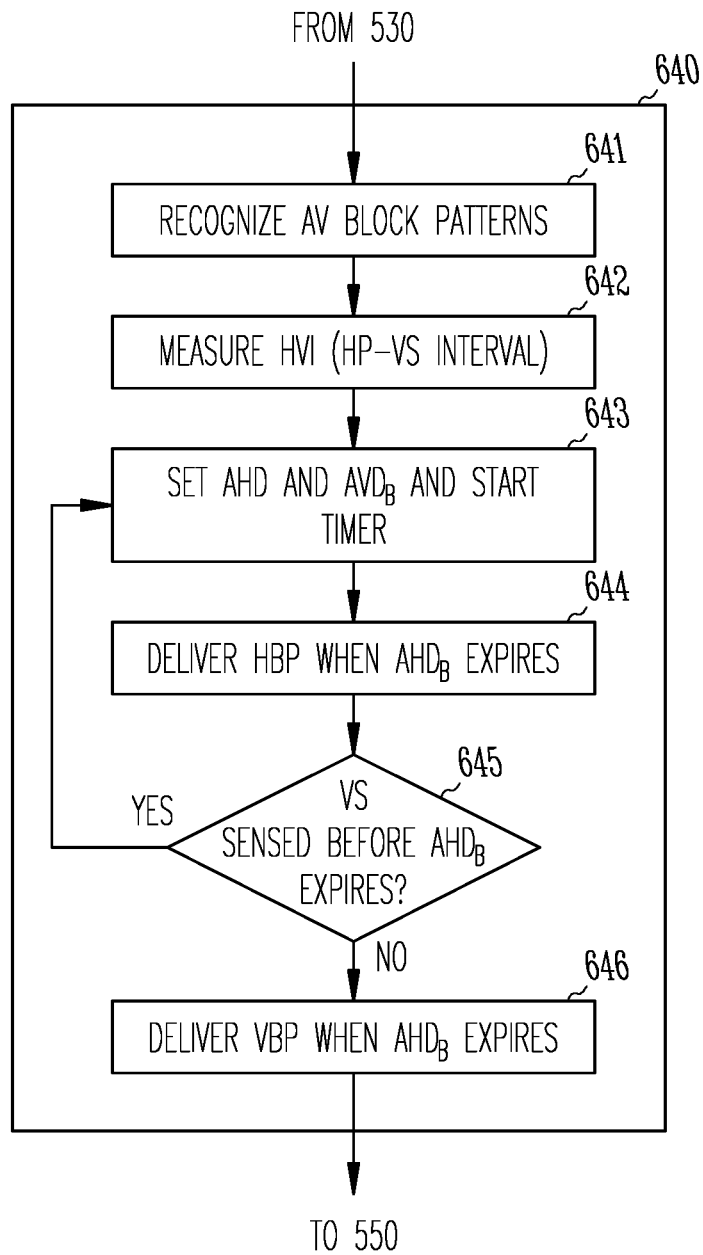
FIG. 6 is a block diagram illustrating an example of a method of timing the HBP or VBP using an AV block pattern in the presence of AV conduction abnormality.

FIG. 6 is a block diagram illustrating an example of a method 640 of timing the HBP or VBP in the presence of AV conduction abnormality, such as using an AV block pattern. The method 640 is an embodiment of a portion of the method 500, such as step 540 for delivering HBP and VBP in the presence of AV conduction abnormality. The method 640 may be implemented in and executed by the system 400.

The method 640 begins at 641, where an AV block pattern may be recognized, such as using the AV block pattern recognizer circuit 410. Examples of the AV block pattern may include a first-degree AV block, a second-degree AV block which may further be classified into a Mobitz type I bock or a Mobitz type II block, or a third-degree AV block. Recognition of AV block pattern may be based on AV intervals corresponding to conducted ventricular beats prior to a conduction block to the ventricle. In an example, a first-degree AV block may be recognized if a trend of AV interval, or a central tendency of the AV intervals, exceeds a threshold, such as approximately 200 msec. In another example, a Mobitz I block may be recognized by progressive prolongation of AV intervals on consecutive beats followed by a blocked AS event. In yet another example, a Mobitz II block may be recognized by intermittently non-conducted atrial events, not preceded by AV prolongation and not followed by AV shortening.

At 642, a His-to-ventricular interval (HVI) may be determined, such as during a test where HBP is delivered and the resultant ventricular response is detected. At 643, an atrio-Hisian delay (AHD), which controls the timing for delivering HBP, may be set. The AHD may be determined using a difference between a target AVI and the HVI, according to Equation (1) above. The target AVI may be separately and respectively determined for the recognized AV conduction pattern, such as Mobitz type I or Mobitz type II block. By way of non-limiting example, the target AVI for Mobitz type I block may be a shortest interval $(AVI_{min})$ among a plurality of progressively prolonged AV intervals prior to the conduction block to the ventricle. In another example, the target AVI for a Mobitz type II block may be an average $(AVI_{avg})$ or other central tendency of the plurality of conducted AV intervals prior to a conduction block. Also at 643, an atrioventricular interval $(AVD_B)$ for ventricular backup pacing (VBP) may be determined, such as according to Equation (2). Respective timers for HBP and VBP may then start from each atrial sensed (AS) or paced (AP) event.

At 644, when AHD expires, HBP may be delivered to stimulate the His bundle or another portion of the physiologic conduction pathway. The manner of HBP delivery may be dependent on the AV block pattern. In an example, in the presence of a relatively consistent P to QRS ratio, the HBP may be delivered only at the time that P wave is dropped (not conducted through). This may promote the intrinsic AV conduction prior to the dropped P wave. In another example, when Mobitz type II block is recognized, a statistic of conducted beats prior to a conduction block to the ventricle may be determined, such as an average number of conducted beats before a block occurs during Mobitz type II block. HBP pulses may be delivered for a first number (M) of consecutive cardiac cycles, followed by withholding the HBP delivery for a second number (N) of cardiac cycles to promote intrinsic AV conductions. Delivering the HBP for M cardiac cycles during which block or substantial AV conduction disturbance may occur may improve cardiac function. The second number N may correspond to the average number of conducted beats with no significant AV conduction disturbance (e.g., short AV intervals), such that the withholding of HBP may promote intrinsic conduction and ventricular activation.

Following the HBP delivery, ventricular activity is monitored throughout the $AVD_B$. At 645, if a VS event is sensed before expiration of the $AVD_B$, then no VBP is to be delivered, and the timers for HBP and VBP may be reset at 643. If no VS event is sensed upon expiration of the $AVD_B$, then at 646, VBP is delivered at the expiration of the $AVD_B$.

Figure 7:
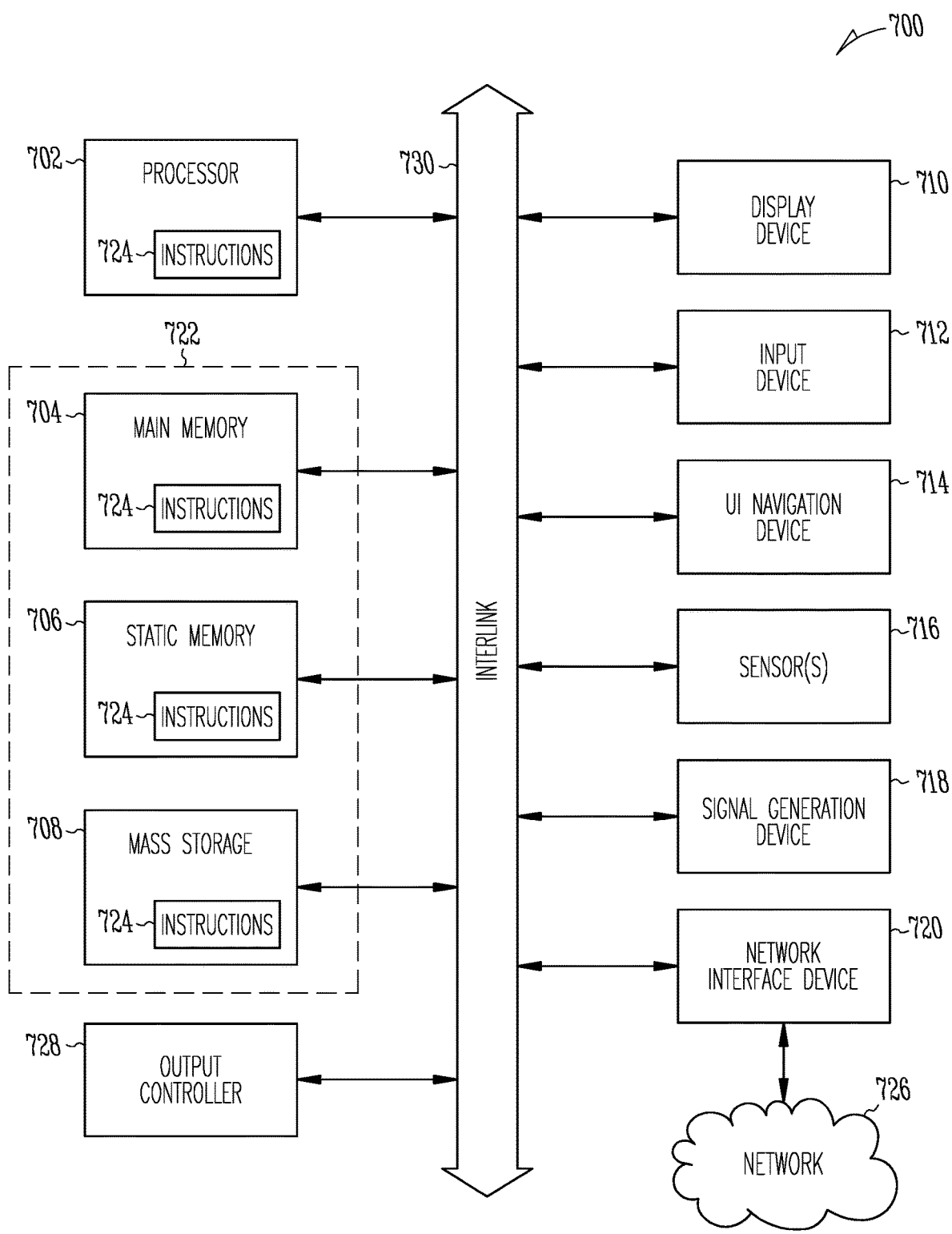
FIG. 7 illustrates a block diagram of an example machine upon which any one or more of the techniques (e.g., methodologies) discussed herein may perform.

FIG. 7 illustrates a block diagram of an example machine 700 upon which any one or more of the techniques (e.g., methodologies) discussed herein may perform. Portions of this description may apply to the computing framework of one or more of the medical devices described herein, such as the IMD, the external programmer, etc.

Examples, as described herein, may include, or may operate by, logic or a number of components, or mechanisms in the machine 700. Circuitry (e.g., processing circuitry) is a collection of circuits implemented in tangible entities of the machine 700 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, movable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 700 follow.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 700 may include a hardware processor 702 (e.g., a central processing unit (CPU), a graphics processing unit (GPU), a hardware processor core, or any combination thereof), a main memory 704, a static memory (e.g., memory or storage for firmware, microcode, a basic-input-output (BIOS), unified extensible firmware interface (UEFI), etc.) 706, and mass storage 708 (e.g., hard drive, tape drive, flash storage, or other block devices) some or all of which may communicate with each other via an interlink (e.g., bus) 730. The machine 700 may further include a display unit 710, an alphanumeric input device 712 (e.g., a keyboard), and a user interface (UI) navigation device 714 (e.g., a mouse). In an example, the display unit 710, input device 712, and UI navigation device 714 may be a touch screen display. The machine 700 may additionally include a signal generation device 718 (e.g., a speaker), a network interface device 720, and one or more sensors 716, such as a global positioning system (GPS) sensor, compass, accelerometer, or one or more other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 702, the main memory 704, the static memory 706, or the mass storage 708 may be, or include, a machine-readable medium 722 on which is stored one or more sets of data structures or instructions 724 (e.g., software) embodying or utilized by any one or more of the techniques or functions described herein. The instructions 724 may also reside, completely or at least partially, within any of registers of the processor 702, the main memory 704, the static memory 706, or the mass storage 708 during execution thereof by the machine 700. In an example, one or any combination of the hardware processor 702, the main memory 704, the static memory 706, or the mass storage 708 may constitute the machine-readable medium 722. While the machine-readable medium 722 is illustrated as a single medium, the term "machine-readable medium" may include a single medium or multiple media (e.g., a centralized or distributed database, and/or associated caches and servers) configured to store the one or more instructions 724.

The term "machine-readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may be further transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical-device system, comprising:
an atrioventricular (AV) conduction monitor circuit configured to detect an indication of a presence or absence of AV conduction abnormality of a heart of a subject; and
a control circuit configured to control an electrostimulation circuit configured to generate His-bundle pacing (HBP) pulses, and to provide a control signal to:
in response to a detected indication of presence of AV conduction abnormality of the heart, deliver HBP pulses at expiration of an atrio-Hisian delay (AHD) to stimulate a physiologic conduction pathway of the heart, sense a ventricular activation during a second atrioventricular delay (AVD), and time delivery of ventricular backup pacing (VBP) at expiration of the second AVD if no ventricular activation is sensed during the second AVD, wherein both the AHD and the second AVD begin at an atrial sensed event or an atrial paced event, and the second AVD is longer than the AHD; and
in response to a detected indication of absence of AV conduction abnormality of the heart, withhold delivery of HBP pulses.

2. The system of claim 1, including the electrostimulation circuit, wherein, in response to the detected indication of absence of AV conduction abnormality:
the control circuit is configured to sense an intrinsic ventricular activation during a first atrioventricular delay (AVD) that begins at the atrial sensed event or the atrial paced event; and
the electrostimulation circuit is configured to deliver ventricular demand pacing (VDP) at expiration of the first AVD if no intrinsic ventricular activation is sensed during the first AVD.

3. The system of claim 1, wherein the control circuit is configured to determine a frequency of VBP delivery over a specified time period, and to optimize an HBP configuration for stimulating the physiologic conduction pathway if the determined VBP frequency exceeds a threshold.

4. The system of claim 3, wherein the control circuit is configured to optimize the HBP configuration including:
verifying a HBP capture status;
extending the second AVD if the HBP capture status is a selective or non-selective His bundle capture; and
adjusting an HBP parameter if the HBP capture status is a para-Hisian capture or a loss of capture.

5. The system of claim 4, wherein the control circuit is configured to perform a threshold test to determine an HBP threshold, and to adjust the HBP parameter using the determined HBP threshold.

6. The system of claim 4, wherein adjusting the HBP parameter includes altering a pacing site at the physiologic conduction pathway for delivering the HBP pulses if the HBP capture status is a para-Hisian capture or a loss of capture.

7. The system of claim 3, wherein the AV conduction monitor circuit is configured to periodically assess AV conduction status if the frequency of VBP falls below the threshold, the assessment including detecting the indication of presence or absence of AV conduction abnormality.

8. The system of claim 1, wherein:
the AV conduction monitor circuit is configured to detect the indication of presence or absence of AV conduction abnormality using a sensed AV interval ($AVI_S$) from an atrial sensed event, or a paced AV interval ($AVI_P$) from an atrial paced event; and the control circuit is configured to control the electrostimulation circuit to:
in response to an indication of presence of AV conduction abnormality, deliver the HBP pulses at expiration of a sensed atrio-Hisian delay ($AHD_S$) that begins at the atrial sensed event, or at expiration of a paced atrio-Hisian delay ($AHD_P$) that begins at the atrial paced event; and
in response to an indication of absence of AV conduction abnormality, withhold delivery of the HBP pulses, and deliver ventricular demand pacing (VDP) at expiration of a sensed atrioventricular delay that begins at the atrial sensed event, or at expiration of a paced atrioventricular delay that begins at the atrial paced event.

9. The system of claim 1, wherein the AV conduction monitor circuit is configured to detect an AV block pattern, and the control circuit is configured to time the delivery of HBP pulses in accordance with the detected AV block pattern.

10. The system of claim 9, wherein:
the AV conduction monitor circuit is configured to determine a target AV interval (AVI) corresponding to the detected AV block pattern using a plurality of AV intervals prior to a conduction block to a ventricle of the heart; and
the control circuit is configured to determine an atrio-Hisian delay (AHD) using the target AVI and a His-to-ventricular interval (HVI), and to time the delivery of the HBP pulses at expiration of the determined AHD.

11. The system of claim 10, wherein the AV block pattern is a Mobitz type I block, and the target AVI is a shortest interval among a plurality of progressively prolonged AV intervals prior to the conduction block to the ventricle.

12. The system of claim 10, wherein the AV block pattern is a Mobitz type II block, and wherein:
the AV conduction monitor circuit is configured to generate a statistic of conducted beats prior to a conduction block to the ventricle; and
the control circuit is configured to control the electrostimulation circuit to deliver the HBP pulses for a first number of consecutive cardiac cycles followed by withholding the HBP delivery for a second number of cardiac cycles, the first and second numbers each determined using the generated statistic of conducted beats.

13. The system of claim 10, wherein the control circuit is further configured to determine the second AVD using the target AVI.

14. A method for pacing a physiologic conduction pathway including a His bundle or a bundle branch of a heart, the method comprising:
detecting an indication of presence or absence of AV conduction abnormality;
in response to an indication of presence of AV conduction abnormality, delivering HBP pulses at expiration of an atrio-Hisian delay (AHD) to stimulate the physiologic conduction pathway, sensing a ventricular activation during a second atrioventricular delay (AVD), and delivering ventricular backup pacing (VBP) at expiration of the second AVD if no ventricular activation is sensed during the second AVD, wherein both the AHD and the second AVD begin at an atrial sensed event or an atrial paced event, and the second AVD is longer than the AHD; and
in response to an indication of absence of AV conduction abnormality, withholding delivery of the HBP pulses, and delivering ventricular demand pacing (VDP) at expiration of a first AVD if no intrinsic ventricular activation is sensed during the first AVD.

15. The method of claim 14, comprising:
determining a frequency of VBP delivery over a specified time period; and
optimizing an HBP configuration for stimulating the physiologic conduction pathway if the determined VBP frequency exceeds a threshold.

16. The method of claim 15, wherein optimizing the HBP configuration includes:
verifying a HBP capture status;
extending the second AVD if the HBP capture status is a selective or non-selective His bundle capture; and
adjusting an HBP parameter if the HBP capture status is a para-Hisian capture or a loss of capture.

17. The method of claim 16, wherein adjusting the HBP parameter includes altering a pacing site at the physiologic conduction pathway for delivering the HBP pulses if the HBP capture status is a para-Hisian capture or a loss of capture.

18. The method of claim 14, comprising:
detecting an AV block pattern; and
delivering the HBP pulses in accordance with the detected AV block pattern.

19. The method of claim 18, wherein the AV block pattern is a Mobitz type I block, and the method comprising:
determining a target AV interval (AVI) corresponding to a shortest interval among a plurality of progressively prolonged AV intervals prior to a conduction block to a ventricle of the heart;
determining an atrio-Hisian delay (AHD) using the target AVI and a His-to-ventricular interval (HVI); and
delivering the HBP pulses at expiration of the determined AHD.

20. The method of claim 18, wherein the AV block pattern is a Mobitz type II block, and the method comprising:
generating a statistic of conducted beats prior to a conduction block to a ventricle of the heart; and
delivering the HBP pulses for a first number of consecutive cardiac cycles followed by withholding the HBP delivery for a second number of cardiac cycles, the first and second numbers each determined using the generated statistic of conducted beats.

* * * * *